US012741130B2

(12) United States Patent
Xia

(10) Patent No.: US 12,741,130 B2
(45) **Date of Patent: *Sep. 22, 2026**

(54) TATTOO PRACTICE DEVICE AND COLORING ASSEMBLY IN TATTOO PRACTICE DEVICE

(71) Applicant: Tingting Xia, Suzhou (CN)

(72) Inventor: Tingting Xia, Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/390,717

(22) Filed: Nov. 17, 2025

(65) Prior Publication Data

US 2026/0069845 A1 Mar. 12, 2026

Related U.S. Application Data

(63) Continuation of application No. 18/604,569, filed on Mar. 14, 2024, now Pat. No. 12,496,437, which is a continuation of application No. PCT/CN2022/119794, filed on Sep. 20, 2022.

(30) Foreign Application Priority Data

Sep. 24, 2021 (CN) .......................... 202111121379.8
Sep. 8, 2022 (CN) .......................... 202222394997.6

(51) Int. Cl.
*A61M 37/00* (2006.01)
*B41J 2/31* (2006.01)
*G09B 19/04* (2006.01)
*G09B 19/24* (2006.01)

(52) U.S. Cl.
CPC ............ *A61M 37/0076* (2013.01); *B41J 2/31* (2013.01); *G09B 19/24* (2013.01)

(58) Field of Classification Search
CPC .......... G09B 19/24; G09B 23/285; B41J 2/31; A61M 37/0076; A61M 37/00; A61M 37/0084
See application file for complete search history.

(56) References Cited

U.S. PATENT DOCUMENTS

2023/0069394 A1* 3/2023 Romero ................. G09B 19/24

* cited by examiner

*Primary Examiner* — Katherine M Shi

(57) ABSTRACT

A tattoo practice device includes a coloring portion, a connecting portion, and a sleeve. The coloring portion includes a coloring rod. The coloring rod is a coloring core configured to apply a color on a drawing medium; the coloring rod includes a non-piercing distal end. One end of the connecting portion is connected to the coloring portion, the connecting portion is linked with the coloring portion, and the sleeve is sleeved on a periphery of the connecting portion. The connecting portion is configured to move in a first direction along a central axis of the sleeve, so that the coloring core is close to the drawing medium and color the drawing medium; and the connecting portion is configured to move in a second direction opposite to the first direction along the central axis of the sleeve, so that the coloring core moves away from the drawing medium.

18 Claims, 13 Drawing Sheets

TATTOO PRACTICE DEVICE AND COLORING ASSEMBLY IN TATTOO PRACTICE DEVICE

CROSS-REFERENCE TO RELATED APPLICATIONS

This application is a continuation of the U.S. patent application Ser. No. 18/604,569, filed on Mar. 14, 2024. The U.S. patent application Ser. No. 18/604,569 is a continuation of PCT/CN2022/119794, with a title of Semi-permanent Microblading Practice Apparatus and Pen Using Practice Apparatus, filed Sep. 20, 2022, which claims priority benefit to Chinese Patent Application No. 202222394997.6, filed on Sep. 8, 2022 and priority benefit to Chinese Patent Application No. 202111121379.8, filed on Sep. 24, 2021, with the China National Intellectual Property Administration (CNIPA), all of which are incorporated herein by reference in their entirety.

TECHNICAL FIELD

The present invention relates to the technical field of teaching and training aids of the tattoo industry, and in particular, to a tattoo practice device applicable to tattoo practice and design and a coloring assembly arranged in the tattoo practice device.

BACKGROUND

Tattooing is a skin-breaking and coloring beauty method, in which a tool is used to puncture a body skin or a facial skin and deliver pigment to a specific depth to retain for a period of time. Because an ideal tattoo state is to have less skin damage and more color retention, the operation principle of the mainstream tattoo tool is mostly using the tip of the tool to break a skin and deliver pigment in dots. Whether the pattern is a line pattern or a block pattern, it is formed by arranging several colored points.

Since tattooing is to draw on a human skin, it is almost impossible to erase or modify any drawing mistake. Based on this, to obtain good tattoo works, all tattoo trainees, skilled tattooists, and tattoo trainers need a large amount of drawing practice other than human skin hands-on operation, to improve the drawing capability to ensure quality of tattoo works, thereby reducing or avoiding the drawing mistakes.

Because there are no specialized tattoo drawing practice tools in the industry today, tattooists use common drawing tools such as pencils, brushes, pens, and gel ink pens for tattoo drawing practice. Compared with a professional tattoo tool, a nib (coloring portion) for coloring of ordinary stationery is static relative to the hand during use. A nib (coloring portion) for coloring of the tattoo tool (manually operated or electrically operated) performs a striking movement reciprocating up and down relative to the hand during use.

Therefore, there is a large difference between the drawing tool used for tattoo needling or tattoo design drawing practice and the professional tool for tattoo hands-on operation. The former is static, and the latter is dynamic in operation principles during tattoo coloring, they differ in sense of use and the operation precautions, and in the entire drawing process, they differ the way holding gesture, strength control, and speed of handling the pen.

Therefore, there is a large difference between the existing practice tool for tattoo needling or tattoo design drawing and the tattoo tool used during hands-on operation. Drawing experience of using the ordinary stationery to practice drawing mismatches drawing experience required during hands-on operation, making it difficult for a beginner to acquire tattooing experience, and causing a significant discrepancy between a tattoo practice effect and a hands-on operation effect. Drawing well during practice does not mean doing well during hands-on operation. The existing feel and muscle memory practiced by using static drawing tools cannot adapt to a dynamic movement of a tattoo tool during hands-on coloring. The tattoo practice involves much useless work, the practice mismatches the hands-on operation seriously, the learning period is long, and the completion rate is low, causing a low excellent rate of hands-on tattooing on human skin.

Therefore, a new technical solution is urgently needed to resolve the problem in the related art.

SUMMARY

There is a large difference between the existing practice tool for tattoo needling or tattoo design drawing and the tattoo tool used during hands-on operation. Drawing experience of using the ordinary stationery to practice drawing mismatches drawing experience required during hands-on operation, making it difficult for a beginner to acquire tattooing experience, and causing a significant discrepancy between a tattoo practice effect and a hands-on operation effect. Drawing well during practice does not mean doing well during hands-on operation. The existing feel and muscle memory practiced by using static drawing tools cannot adapt to a dynamic movement of a tattoo tool during hands-on coloring. The tattoo practice involves much useless work, the practice mismatches the hands-on operation seriously, the learning period is long, and the completion rate is low, causing a low excellent rate of hands-on tattooing on human skin. To resolve the problem in the related art, the present invention provides a tattoo practice device. The technical solutions adopted are as follows:

The present disclosure provides a tattoo practice device, including a coloring portion, a connecting portion, and a sleeve. The coloring portion includes a coloring rod, wherein the coloring rod is a coloring core configured to apply a color on a drawing medium; the coloring rod includes a non-piercing distal end. One end of the connecting portion is connected to the coloring portion, the connecting portion is linked with the coloring portion, and the sleeve is sleeved on a periphery of the connecting portion. The connecting portion is configured to move in a first direction along a central axis of the sleeve, so that the coloring core is close to the drawing medium and color the drawing medium; and the connecting portion is configured to move in a second direction opposite to the first direction along the central axis of the sleeve, so that the coloring core moves away from the drawing medium.

The present disclosure further provides a coloring assembly, configured to be arranged in a tattoo practice device, the coloring assembly includes: a coloring portion, including a coloring rod configured to apply a color on a drawing medium; the coloring rod includes a non-piercing distal end; a connecting portion connected to the coloring rod; a splitting portion with a though hole for movably mounting the connecting portion; an elastic member connected to at least one of the connecting portion, the coloring portion, or the splitting portion. The coloring portion and the connecting portion are integrally formed as a one-piece structure or are two separatable elements; the connecting portion is movably received in the through hole of the splitting portion; when the connecting portion is driven by an external force to move along a central axis of the coloring portion, the elastic member is elastically deformed to generate a restoring force; and when the external force applied to the connecting portion is released, the elastic member is configured to apply the restoring force to cause the connecting portion to restore to an initial position.

The present disclosure further provides a tattoo practice device, including a coloring portion, a connecting portion, and a sleeve. The coloring portion includes a plurality of coloring rods. Each of the plurality of coloring rods is a coloring core configured to apply a color on a drawing medium; each of the plurality of coloring rods includes a non-piercing distal end. One end of the connecting portion is connected to the coloring portion, the connecting portion is linked with the coloring portion, and the sleeve is sleeved on a periphery of the connecting portion. The connecting portion is configured to move in a first direction along a central axis of the sleeve, so that the coloring core is close to the drawing medium and color the drawing medium; and the connecting portion is configured to move in a second direction opposite to the first direction along the central axis of the sleeve, so that the coloring core moves away from the drawing medium.

BRIEF DESCRIPTION OF THE DRAWINGS

To more clearly describe embodiments of the present invention or the technical solutions in the related art, the accompanying drawings used in the description of the embodiments or the related art will be briefly introduced below. The accompanying drawings in the following description are merely some embodiments of the present invention. For those of ordinary skill in the art, other accompanying drawings can be obtained based on these accompanying drawings without creative efforts.

Figure 1:
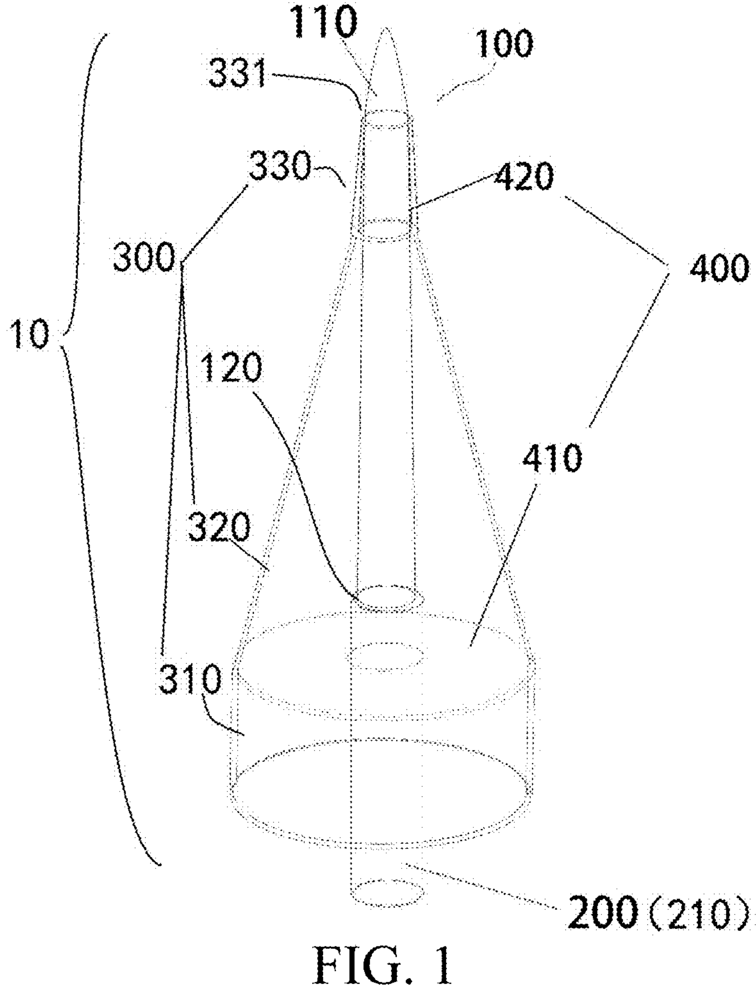
FIG. 1 is a schematic structural diagram of a tattoo practice device according to an embodiment of the present invention, wherein a coloring portion includes a coloring rod.

Wherein 10—tattoo practice device;

100—coloring portion; 110—coloring rod; 120—mounting base; 200—connecting portion; 210—connecting rod;

300—sleeve; 310—fastening end; 320—middle connecting tube; 321—dent; 330—outlet end; 331—outlet;

400—limiting structure; 410—limiting hole; 420—limiting tube;

500—elastic member;

600—angle clamping member; 610—clamping plate;

700—electric pen; 710—operation penholder; 720—pitch adjustment component; 730—top rod;

101—paper; 201—resilient anti-splitting member; 202—anti-splitting hole; 800—splitting portion; 900—tattoo needle; and 901—artificial skin.

DETAILED DESCRIPTION

The following clearly and completely describes the technical solutions in embodiments of the present invention with reference to the accompanying drawings in the embodiments of the present invention. Apparently, the described embodiments are merely some but not all of the embodiments of the present invention. Based on the embodiments of the present invention, all other embodiments obtained by a person of ordinary skill in the art without creative efforts shall fall within the protection scope of the present invention.

In the description of the present invention, it should be understood that orientation or position relationships indicated by the terms such as “over”, “below”, “top”, “bottom”, “inner”, and “outer” are based on orientation or position relationships shown in the accompanying drawings, and are used only for ease and brevity of illustration and description for the present invention, rather than indicating or implying that the mentioned apparatus or component need to have a particular orientation or need to be constructed and operated in a particular orientation. Therefore, such terms should not be construed as limiting of the present invention. In the descriptions of the present invention, "a plurality of" means two or more, unless otherwise definitely and specifically limited.

In the present invention, unless explicitly specified or limited otherwise, the terms such as "mounted", "connected", "connection", and "fixed" should be understood broadly, for example, which may be a fixed connection, a detachable connection, or an integral connection; or the connection may be a mechanical connection or an electrical connection; or the connection may be a direct connection, an indirect connection through an intermediate, for example, a mechanical abutment connection or contact connection through abutment, contact, and the like, or may be internal communication between two elements or an interaction relationship between two elements. A person of ordinary skill in the art can understand specific meanings of the foregoing terms in the present invention according to a specific situation.

A gist of the present invention is further described below with reference to the accompanying drawings and the embodiments.

Embodiment 1

To implement efficient and accurate coloring on skin, especially when it is necessary to implement block or strip coloring, the existing tattoo tool is mainly formed by fixing one or more metal needle wires with one end sharpened to a needle handle, putting a spring on the needle handle, and then putting the needle handle in a sleeve. This tattoo tool is fixed to a tattoo pen through one end of the sleeve, and under power transmission, the needle handle drives the needle wire to reciprocate along a central axis of the sleeve to complete a skin-breaking and coloring operation.

It may be learned that when the tattoo tool is used to break and color the skin, the needle wire of the tattoo tool used by a tattooist is always dynamic, with the needle wire reciprocating relative to the sleeve. In this dynamic operating condition, it is difficult for the tattooist to acquire operating experience. Therefore, to perform hands-on tattooing on a human body, the tattooist needs to undergo a lot of training. However, because there are no specialized tattoo drawing practice tools in the industry today, tattooists use common drawing tools such as pencils, brushes, pens, and gel ink pens for tattoo drawing practice. Compared with a professional tattoo tool, a nib (coloring portion) for coloring of ordinary stationery is static relative to the hand during use. A nib (coloring portion) for coloring of the tattoo tool (manually operated or electrically operated) performs a striking movement reciprocating up and down relative to the hand during use. Therefore, there is a large difference between the drawing tool used for tattoo needling or tattoo design drawing practice and the professional tool for tattoo hands-on operation. The former is static and the latter is dynamic in operation principles during tattoo coloring, they differ in sense of use and the operation precautions, and in the entire drawing process, they differ the way holding gesture, strength control, and speed of handling the pen.

Therefore, tattoo drawing experience of using the ordinary stationery to practice drawing mismatches drawing experience required during hands-on operation, making it difficult for a beginner to acquire tattooing experience, and causing a significant discrepancy between a tattoo practice effect and a hands-on operation effect. Drawing well during practice does not mean doing well during hands-on operation. The existing feel and muscle memory practiced by using static drawing tools cannot adapt to a dynamic movement of a tattoo tool during hands-on coloring. The tattoo practice involves much useless work, the practice mismatches the hands-on operation seriously, the learning period is long, and the completion rate is low, causing a low excellent rate of hands-on tattooing on human skin.

To resolve the problem in the related art, the present invention provides a tattoo practice device. FIG. 1 is a schematic structural diagram of a tattoo practice device. The tattoo practice device 10 includes a coloring portion 100, a connecting portion 200, and a sleeve 300. The coloring portion 100 includes one or more coloring rods 110, and the more coloring rods 110 are arranged in a dot matrix (the coloring portion 100 shown in FIG. 1 includes one coloring rod 110). One end of the connecting portion 200 is connected to the coloring portion 100, the connecting portion 200 is linked with the coloring portion 100, and the sleeve 300 is sleeved on a periphery of the connecting portion 200. When the connecting portion 200 is driven to move in a first direction along a central axis of the sleeve 300, the coloring rod 110 is driven to be close to a drawing medium and color the drawing medium. When the connecting portion 200 is driven to move in a second direction opposite to the first direction along the central axis of the sleeve 300, the coloring rod 110 is driven to move in a direction away from the drawing medium. Therefore, the tattoo practice device 10 provided in the present invention restores a dynamic operation environment of the tattoo tool in hands-on operation compared with common stationery that the tattooist commonly uses for practice.

In one embodiment, the coloring portion 100 of the tattoo practice device 10 in the present invention may include a mounting base 120 and the coloring rod 110. One or more coloring rods 110 are connected to the mounting base 120. The coloring rods 110 are arranged on the mounting base 120 in a dot matrix to form a bunch, or the coloring rods 110 are arranged on the mounting base 120 in a dot matrix to form at least one row. Dot coloring, line coloring, or block coloring may be involved in practical tattooing. Therefore, there are different types of tattoo tools corresponding to different coloring requirements. To adapt to various types of tools, the practice device provided in the present invention may also be randomly transformed into practice devices corresponding to various types of tattoo tools. Corresponding to a line coloring tool, the coloring portion 100 of the tattoo practice device 10 provided in the present invention has a row of coloring rods 110. Corresponding to a block coloring tool, the coloring portion 100 of the tattoo practice device 10 provided in the present invention has a bunch of coloring rods 110.

In some embodiments, a mounting panel and a connecting panel opposite to each other may be arranged on the mounting base 120. The coloring rods 110 are mounted on the mounting panel, a central axis of the coloring rod 110 is perpendicular to the mounting panel, and the connecting panel is connected to the connecting portion 200. The coloring rods 110 are perpendicular to the mounting panel to adapt to a needling operation that perpendicularly pierces the skin for breaking and coloring the skin.

In one embodiment, an end surface of one end of the connecting portion 200 connected to the coloring portion 100 may be directly connected to the coloring rod 110. In this case, the end surface of the connecting portion 200 replaces the function of the mounting base 120. Therefore, the coloring portion 100 and the connecting portion 200 may be in an integral design, or may be in a separate detachable design.

In one embodiment, the coloring rod 110 used in the practice device in the present invention may be any elongated columnar structure. In one case, two end surfaces of the elongated columnar structure have a same shape and a same size, for example, a columnar body with two ends of a same size. In another case, the two end surfaces of the elongated column structures have different shapes and different sizes, and a size of one end surface close to the connecting portion 200 is greater than a size of the other end surface, for example, one end is a cone-like body with an end surface close to the connecting portion 200 as a conical bottom.

In one embodiment, the connecting portion 200 may be a connecting rod 210. One end of the connecting rod 210 is fixedly connected to the connecting panel of the mounting base 120, and an other end of the connecting rod 210 is detachably connected to an external driving member. The external driving member may be a manual pen or an electric pen 700.

In one embodiment, the sleeve 300 in the practice device in the present invention may be a tubular sleeve or a tube-like sleeve. The sleeve 300 includes a fastening end 310, a middle connecting tube 320, and an outlet end 330. The fastening end 310, the middle connecting tube 320, and the outlet end 330 are sequentially connected to form a channel for the connecting portion 200 to reciprocate, and a central axis of the fastening end 310 and a central axis of the middle connecting tube 320 separately coincide with a central axis of the sleeve 300.

In one embodiment, the fastening end 310 is detachably connected to the external driving member. An outlet 331 is provided on the outlet end 330. The connecting portion 200 and the coloring portion 100 arranged at the end of the connecting portion 200 are mounted in the middle connecting tube 320 of the sleeve 300 along the central axis of the sleeve 300. The coloring portion 100 is close to the outlet end 330, the connecting portion 200 reciprocates in the middle connecting tube 320, and the connecting portion 200 drives the coloring rod 110 of the coloring portion 100 to extend out of the outlet 331 or retract into the outlet 331.

Figures 2, 3, 4:
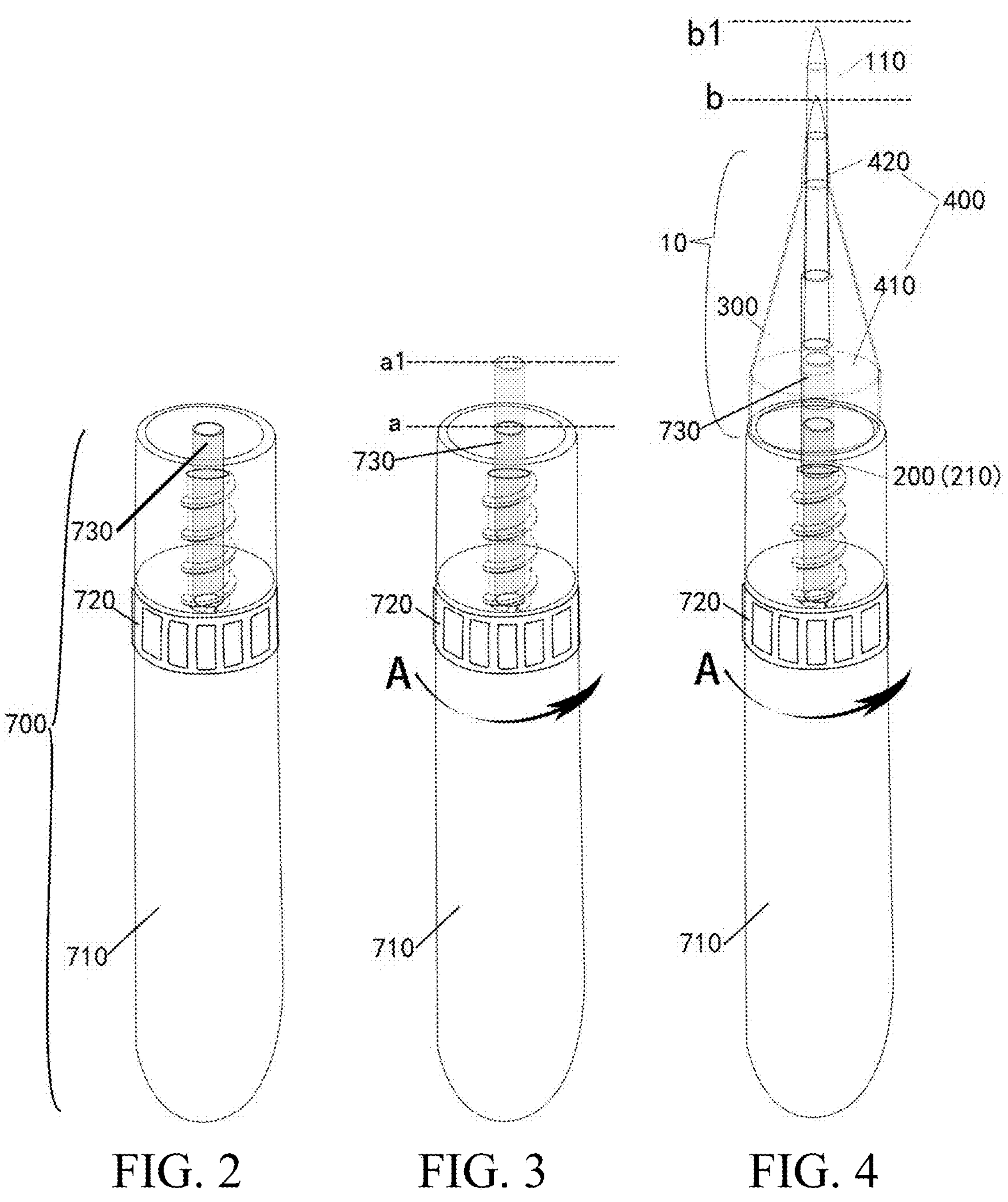
FIG. 2 is a three-dimensional schematic structural diagram of an electric pen.
FIG. 3 is a schematic diagram of a length change of a top rod of the electric pen after a pitch adjustment component of the electric pen shown in FIG. 2 is adjusted, wherein the pitch adjustment component is rotated by a specific degree in a direction A, so that the top rod extends out by a specific length relative to the electric pen.
FIG. 4 is a structural perspective view after the tattoo practice device shown in FIG. 1 and the electric pen shown in FIG. 2 are combined and mounted.

In one embodiment, the external driving member may be an electric pen 700. Referring to FIG. 2, FIG. 3, and FIG. 4, the fastening end 310 of the sleeve 300 of the practice device is connected to one end of an operation penholder 710 of the electric pen 700. A pitch adjustment component 720 and a top rod 730 adjusted by the pitch adjustment component 720 are further arranged at the end of the operation penholder 710 connected to the sleeve 300, and the top rod 730 is connected to an end portion of the connecting portion 200 of the practice device. When the coloring portion 100 is abraded to be shortened, the pitch adjustment component 720 is adjusted (the pitch adjustment component 720 is adjusted through rotation along a direction of an arrow A in FIG. 3), and a length by which the top rod 730 extends out may be changed (referring to FIG. 3, after the pitch adjustment component 720 is adjusted through rotation along the direction of the arrow A, the end surface of the top rod 730 rises from a plane a to a plane al), so that the connecting portion 200 abutting against the top rod 730 is controlled, and then a length by which the coloring portion 100 protrudes from the outlet end 330 of the sleeve 300 is adjusted. Referring to FIG. 4, after the pitch adjustment component 720 is adjusted through rotation along the direction of the arrow A, the top of the coloring rod 110 rises from a plane b to a plane b1, so that the coloring rod 110 of the coloring portion 100 comes into contact with the drawing medium such as paper for practice.

Figure 5:
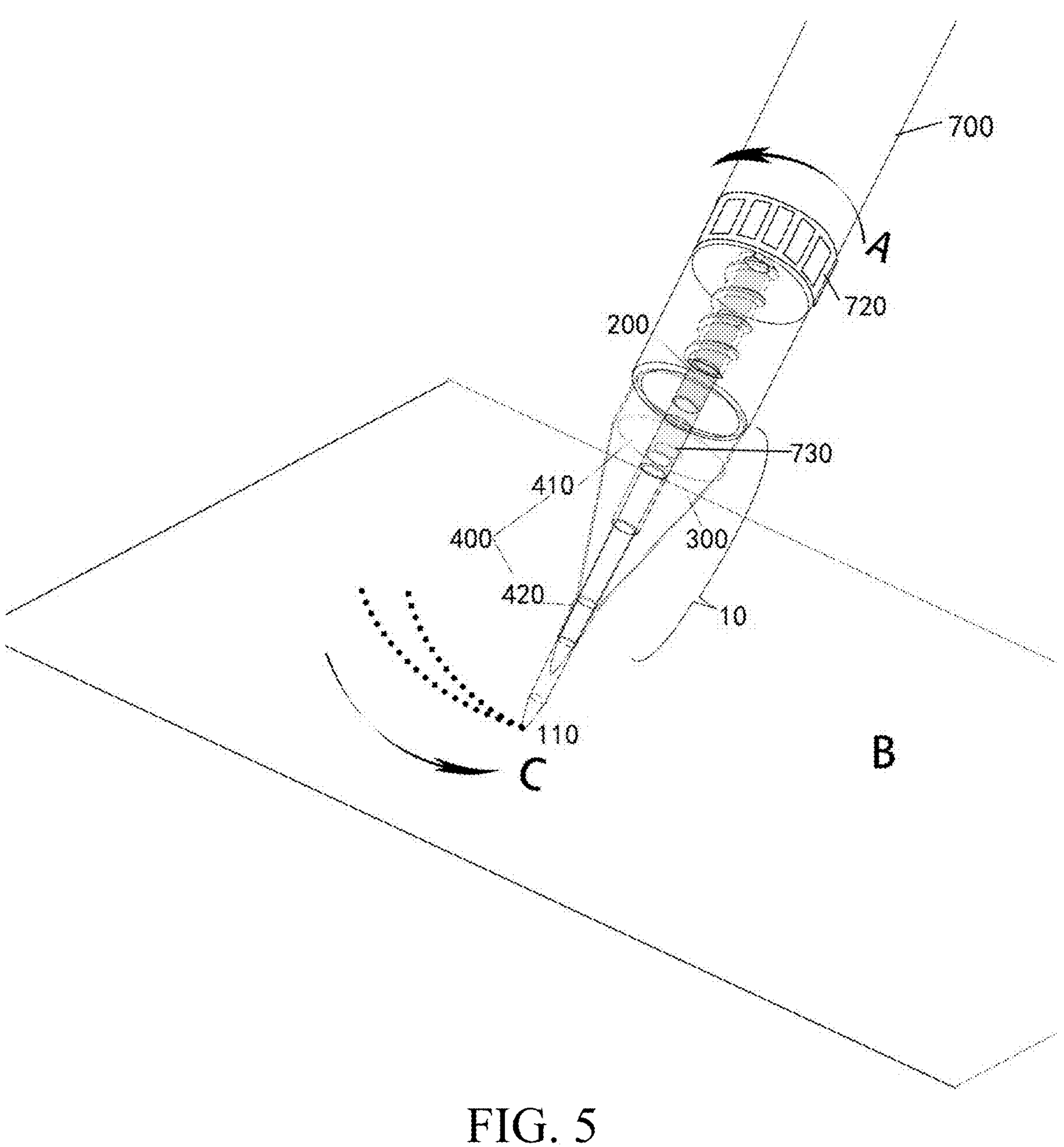
FIG. 5 is a schematic diagram of a use state of using the practice device assembled in FIG. 4 to color a drawing medium B.

Referring to FIG. 4 and FIG. 5, driven by a driving member (motor) of the electric pen 700, when in contact with the drawing medium B such as paper for practice, the coloring rod 110 of the tattoo practice device 10 reciprocates in an axial direction of the sleeve 300. Therefore, when the practice device is used to draw a pattern along a direction of an arrow C, a dotted drawing trajectory occurs, which is consistent with a principle of dotted breaking and coloring the skin by using the tip of the tool when the tattoo tool is used for operation on the human skin. This helps an operator practice the feel and the muscle memory in a dynamic environment immersively, thereby facilitating hands-on operation using a formal tattoo tool seamlessly. The coloring portion 100 shown in FIG. 4 has a coloring rod 110. The coloring rod 110 may be a 2B lead with a thickness of 0.9 mm.

In one embodiment, the sleeve 300 forms a handheld portion of the tattoo practice device 10. A handheld positioning portion may be further arranged on the sleeve 300 that is used as the handheld portion of the tattoo practice device 10. The handheld positioning portion may include one or more finger position points arranged on the middle connecting tube 320 of the sleeve 300. Fingers of the user hold the sleeve 300 in alignment by using the finger position points. That is, during use, the finger position points on the sleeve 300 can instruct the user to hold the sleeve in alignment, helping the user to develop a correct holding gesture, so that the user can adapt to sense of control of the professional tattoo tool during tattoo hands-on operation.

In one embodiment, an elastic ring may be sleeved on the middle connecting tube 320 of the sleeve 300, and then the finger position points are arranged on the elastic ring. The middle connecting tube 320 of the sleeve 300 is a component with a largest area that is held by the user. The arrangement of the elastic ring can improve holding comfort, and increase friction force. The finger position points are arranged on the elastic ring, so that the elastic ring can be replaced conveniently when the finger position points are abraded.

Figures 10, 11:
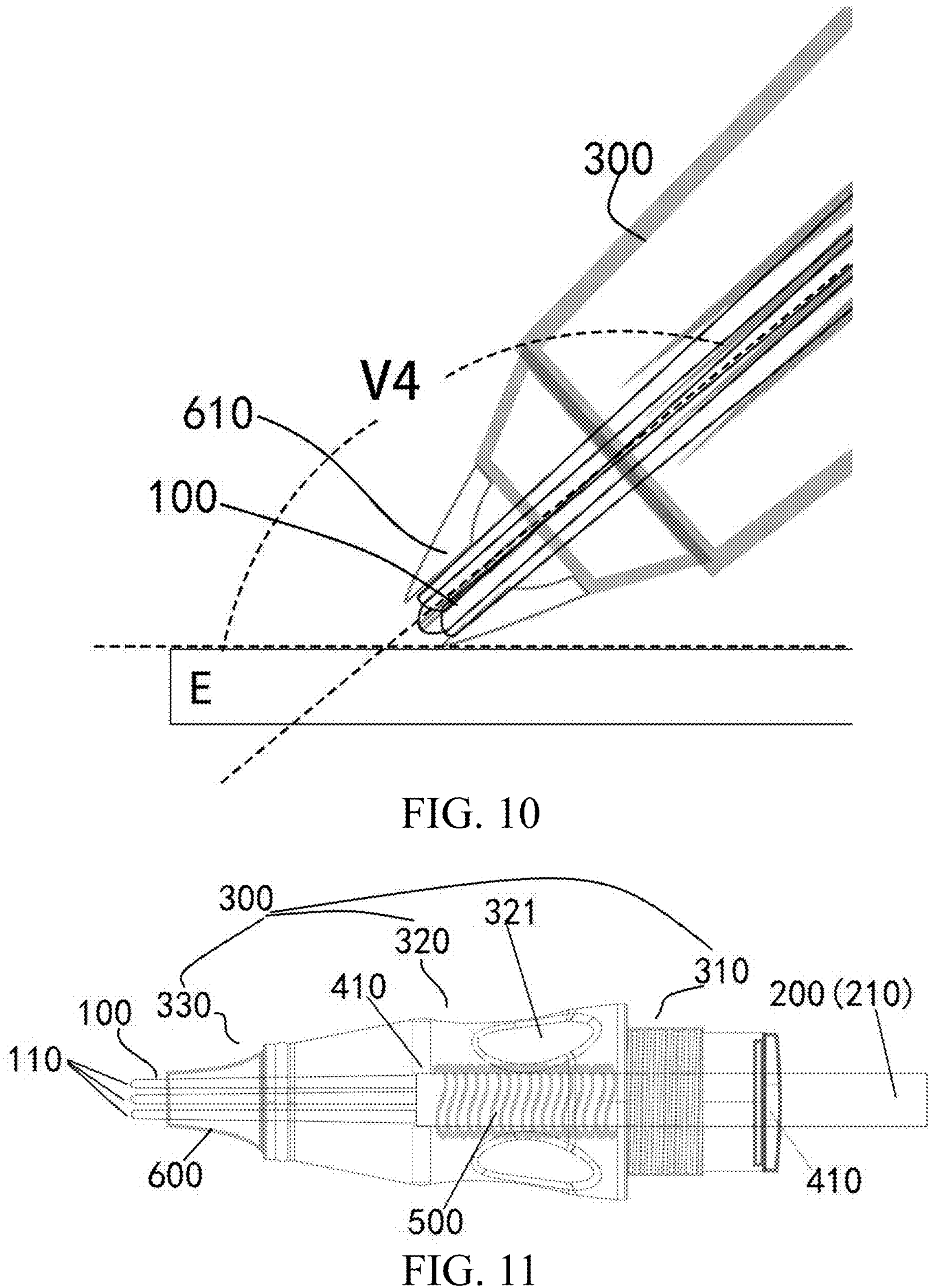
FIG. 10 is a schematic diagram of a use state of using the tattoo practice device shown in FIG. 6 to color a drawing medium E aslant.
FIG. 11 is a schematic structural diagram of a tattoo practice device according to an embodiment of the present invention, where a coloring portion includes three coloring rods arranged in a row.

In one embodiment, one or more dents 321 may be arranged on one finger position point. Referring to FIG. 11, two dents (or more dents may be arranged, but only two dents are shown in the visible part of FIG. 11) are arranged on the middle connecting tube 320 shown in the figure. One dent 321 forms one finger position point, and a shape and an area of the dent may be designed according to a contact area of the finger part at the finger position point when the user holds the sleeve.

In another case, a plurality of small dents may alternatively be arranged in dots to form one finger position point. That is, the plurality of small dents are densely distributed to form a region, the region is one finger position point, and an area and a shape of the finger position point may be designed according to a contact area of the finger part at the finger position point when the user holds the sleeve.

In one embodiment, one or more circles of ring belts may alternatively be arranged on one finger position point, and the ring belt may be a convex ring belt or a concave ring belt. If one circle of convex ring belt encloses one finger position point, a shape and an area enclosed by the convex ring belt may be designed according to a contact area of the finger part at the finger position point when the user holds the sleeve. If a plurality of circles of convex ring belts are distributed in a region, and the region forms one finger position point, the plurality of circles of ring belts may be adjacently distributed densely, or may be sleeved in a form of concentric circles to form a region.

One or more finger position points arranged in the foregoing embodiments may assist the user to hold at a fixed position and master a standard holding gesture, and the dent or the ring belt arranged on the finger position point may be used to form a positioning mark of the finger position point, and increase friction force between the finger and the sleeve, to ensure that the hand tightly holds the pen and the finger is not easy to move.

In one embodiment, a limiting structure 400 may further be arranged on the sleeve 300. The limiting structure 400 is arranged in the middle connecting tube 320 of the sleeve 300, or on the fastening end 310 of the sleeve 300, or on one or more positions on the outlet end 330 of the sleeve 300. When the connecting portion 200 reciprocates along the central axis of the sleeve 300, the connecting portion 200 abuts against the limiting structure 400, and the limiting structure 400 limits swinging of the connecting portion 200 in a cross-sectional direction of the sleeve 300, to cause the connecting portion 200 to drive the coloring rod 110 of the coloring portion 100 to vertically extend out of the sleeve 300 until the coloring rod 110 abuts against the drawing medium, and to cause the connecting portion 200 to drive the coloring rod 110 of the coloring portion 100 to vertically retract from the outside of the outlet into the sleeve 300. The design of the limiting structure 400 can ensure that the coloring portion 100 in the practice device can better enter and exit the sleeve 300, avoiding bending, breaking, or the like. The limiting structure 400 also ensures stability and verticality of the coloring portion 100 entering and exiting the sleeve 300, which can better restore the operation state during practical tattooing.

In one embodiment, referring to FIG. 1, the limiting structure 400 may include a limiting hole 410, and the limiting hole 410 is provided with a through hole (it may be seen from FIG. 1 that the connecting rod 210 runs through the through hole, forming a hole-shaped limiting). When the connecting portion 200 reciprocates along the central axis of the sleeve 300, the connecting portion 200 abuts against the through hole, and the through hole limits the swinging of the connecting portion 200 in the cross-sectional direction of the sleeve 300.

In one embodiment, referring to FIG. 1, the limiting structure 400 may include a limiting tube 420, and the limiting tube 420 has a channel (the limiting tube 420 shown in FIG. 1 may be understood as a functional replacement of the outlet end 330 of the sleeve 300, which simplifies the structural design while maintaining the structural functionality). When the connecting portion 200 reciprocates along the central axis of the sleeve 300, the connecting portion 200 abuts against the channel, and the channel limits the swinging of the connecting portion 200 in the cross-sectional direction of the sleeve 300.

In one embodiment, the limiting structure 400 may alternatively be a limiting baffle, the limiting baffle has a limiting panel, and a plane on which the limiting panel is located forms an angle with or is parallel to a central axis of the connecting portion 200. When the connecting portion 200 reciprocates along the central axis of the sleeve 300, the connecting portion 200 abuts against the limiting panel, and the limiting panel limits the swinging of the connecting portion 200 in the cross-sectional direction of the sleeve 300. In a case, the limiting baffle may be arranged at the outlet of the outlet end of the sleeve. The limiting baffle extends outward from an end surface at the outlet, a panel of the limiting baffle close to a central position of the outlet forms the limiting panel, and an extension direction of the limiting panel forms an angle with or is parallel to the central axis of the connecting rod. In this way, when the coloring portion is driven to extend out from the outlet, the limiting panel may abut against the coloring rod, to limit swinging of the coloring rod in the cross-sectional direction of the sleeve.

Figure 6:
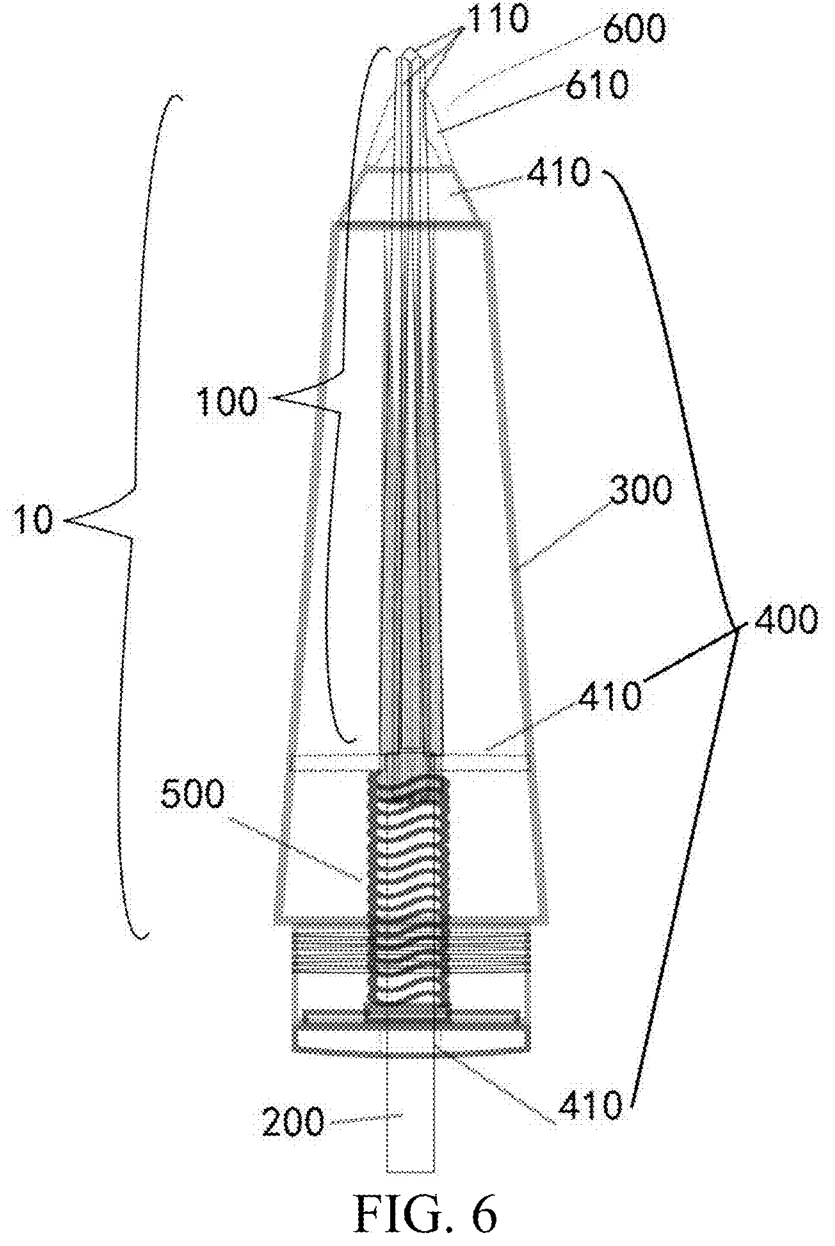
FIG. 6 is a schematic structural diagram of a tattoo practice device according to another embodiment of the present invention, where a coloring portion includes three coloring rods arranged in a dot matrix to form a bunch.

In one embodiment, the limiting structure 400 may alternatively include a limiting support, the limiting support is arranged at an end of or inside the sleeve 300. The limiting support includes one or more sub-supports, one side of the sub-support abuts against the connecting portion 200, and the sub-support limits the swinging of the connecting portion 200 in the cross-sectional direction of the sleeve 300. When the connecting portion 200 reciprocates along the central axis of the sleeve 300, the connecting portion 200 abuts against one side of the sub-support, and the connecting portion 200 is guided to the outlet 331 of the sleeve 300 under abutment of the sub-support. In a case, referring to FIG. 6, an angle clamping member 600 is arranged at the outlet end of the sleeve of the tattoo practice device in FIG. 6. The angle clamping member 600 includes a clamping plate 610 with one end connected to the outlet end and an other end being a free end. Three clamping plates 610 are shown in FIG. 6. The three clamping plates are distributed at the outlet of the sleeve in a triangle, and one of the clamping plates is blocked due to perspective. The clamping plate 610 may also be understood as a limiting support, and this structural functional coverage can simplify the structural design while maintaining the structural functionality of the kit.

It may be learned from the above that the limiting structure 400 arranged on the sleeve 300 may be one or a combination limiting of a plurality of hole-shaped limiting, tube-shaped limiting, baffle limiting, or support limiting.

Embodiment 2

The present invention further provides a tattoo practice device 10. The practice device not only includes the structural features of the practice device according to Embodiment 1, but also may include an elastic member 500. One end of the elastic member 500 is connected to the sleeve 300, and an other end of the elastic member 500 is connected to the connecting portion 200 (a connection relationship between the elastic member 500 and the connecting portion 200 or the sleeve 300 may be any one of abutment connection, hanging connection, sleeve connection, or contact connection, mainly for elastically pulling back the connecting portion 200). FIG. 6 shows a tattoo practice device 10 equipped with an elastic member 500. When the connecting portion 200 is driven by an external force to move to the outlet end 330 of the sleeve 300 close to the coloring portion 100 along the central axis of the sleeve 300, the elastic member 500 elastically deforms to pull the connecting portion 200 back to an initial position. The elastic member 500 may be any one of a spring, a silicone member, and a rubber band.

Therefore, the practice device provided in this embodiment gives a specific automatic resilient function for the kit through mounting of the elastic member 500 and restores the dynamic operation environment. This practice device equipped with the elastic member 500 may be connected to a manual pen.

Embodiment 3

The present invention further provides a tattoo practice device 10. The practice device may not only include the structural features of the practice device according to Embodiment 1, but also include the angle clamping member 600. Referring to FIG. 6, the angle clamping member 600 is arranged at the outlet end 330 of the sleeve 300 close to the coloring portion 100. When the coloring rod 110 is driven with the connecting portion 200 to move to the outlet end 330 of the sleeve 300, an outer wall of the coloring rod 110 abuts against the angle clamping member 600. The angle clamping member 600 may not only limit an inclination angle of the coloring rod 110 relative to the central axis of the sleeve 300, but also limit a length by which the coloring rod 110 protrudes from the angle clamping member 600.

In one embodiment, referring to FIG. 6, the angle clamping member 600 may include one or more clamping plates 610 (three clamping plates 610 are shown in FIG. 6, the three clamping plates are distributed in a triangle at the outlet of the sleeve, and one of the clamping plates is blocked due to perspective), and the clamping plate 610 is arranged on the outlet end 330 of the sleeve 300. When the coloring rod 110 is driven with the connecting portion 200 to move to the outlet end 330 of the sleeve 300, the outer wall of the coloring rod 110 abuts against one side of the clamping plate 610, the clamping plate 610 limits the inclination angle of the coloring rod 110 relative to the central axis of the sleeve 300, and the clamping plate 610 limits the length by which the coloring rod 110 protrudes from the angle clamping member 600. When a plurality of clamping plates 610 are provided, the plurality of clamping plates 610 are evenly arranged on the outlet end 330 of the sleeve 300, and when the coloring rod 110 is driven to move to the outlet end 330 of the sleeve 300, the plurality of clamping plates 610 surround a periphery of the coloring rod 110.

In another embodiment, the angle clamping member 600 may alternatively be a clamping tube, one end of the clamping tube is connected to the outlet end 330 of the sleeve 300, and an other end of the clamping tube is a free open end. When the coloring rod 110 is driven with the connecting portion 200 to move to the outlet end 330 of the sleeve 300, the outer wall of the coloring rod 110 abuts against an inner wall of the clamping tube, the clamping tube limits the inclination angle of the coloring rod 110 relative to the central axis of the sleeve 300, and the clamping tube limits the length by which the coloring rod 110 protrudes from the angle clamping member 600.

Figure 7:
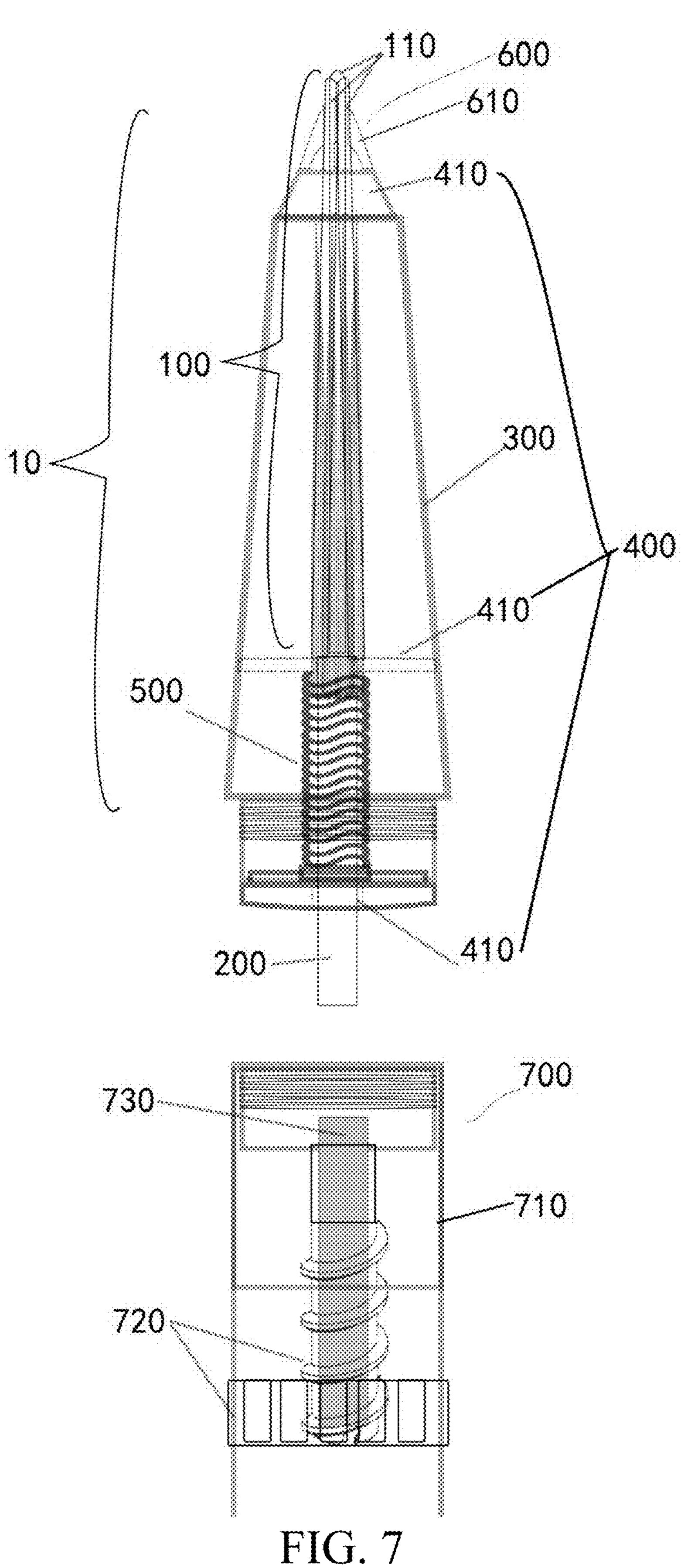
FIG. 7 is a schematic structural diagram when the tattoo practice device shown in FIG. 6 and an electric pen are assembled.

The tattoo practice device according to this embodiment may be combined and mounted with the electric pen or the manual pen, as shown in FIG. 7. Certainly, in another embodiment, the tattoo practice device provided in this embodiment may have the elastic member mentioned in Embodiment 2.

Embodiment 4

This embodiment provides a tattoo practice device 10. Referring to FIG. 6, three coloring rods 110 are arranged in the coloring portion 100 of the tattoo practice device 10. The three coloring rods 110 are arranged in a dot matrix to form a bunch. The three coloring rods 110 may be three soft wooden sticks with ink sac. The kit is further provided with three limiting holes 410, a spring, and an angle clamping member 600. The angle clamping member 600 is a clamping plate 610.

Referring to FIG. 7, the practice device may be mounted on an electric pen 700, which is the same as the electric pen 700 shown in FIG. 2, FIG. 3, and FIG. 4. The electric pen 700 shown in FIG. 7 has a pitch adjustment component 720, and a changeable length of a top rod 730 of the pitch adjustment component 720 extending out is adjusted, to control the connecting portion 200 connected to the top rod 730, thereby adjusting the length by which the coloring rod 110 protrudes from the angle clamping member 600.

Figure 8:
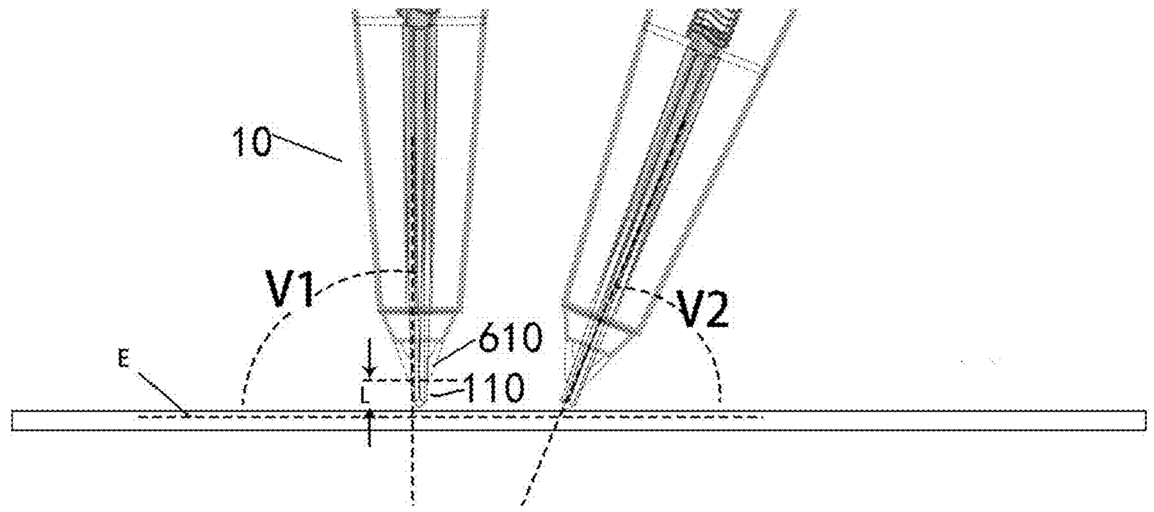
FIG. 8 is a schematic diagram of a use state of using the tattoo practice device shown in FIG. 6 to color a drawing medium E from different angles.

The best coloring technique for tattooing is vertically piercing the skin by using a tattoo tool. A higher verticality indicates a better tattoo effect, as shown in FIG. 8. An angle between the coloring rod 110 of a practice device 10 shown in FIG. 8 and a drawing medium E is V1. When V1 is equal to or infinitely close to 90 degrees, the verticality is higher, which is closer to the best coloring technique required in the tattoo industry. If a length L by which the coloring rod 110 protrudes from the angle clamping member 600 is longer, a requirement for the angle between the coloring rod 110 and the drawing medium is lower. In other words, drawing and coloring may also be performed when an angle V2 between the coloring portion 100 and the drawing medium E is far from 90 degrees.

Figure 9:
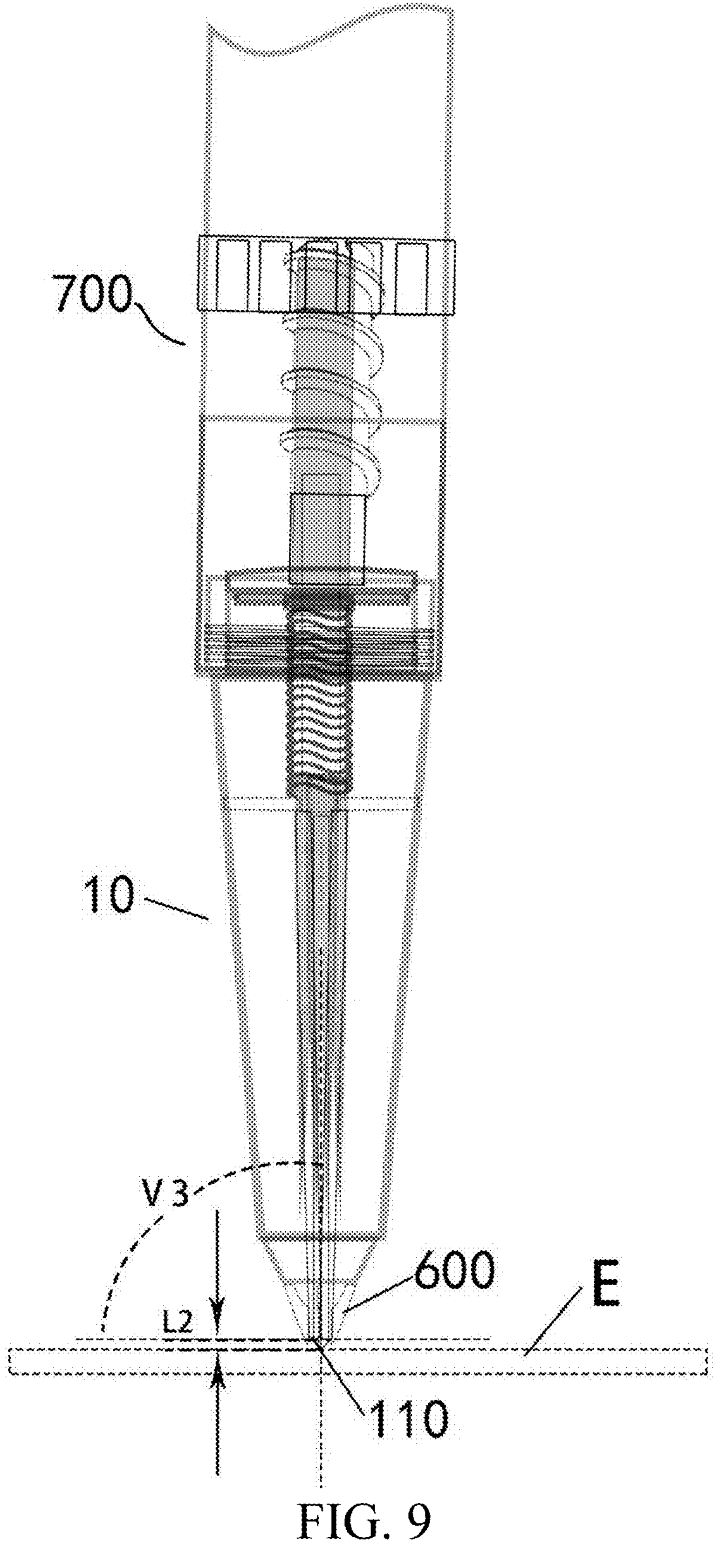
FIG. 9 is a schematic diagram of a use state of using the tattoo practice device shown in FIG. 6 to color a drawing medium E perpendicularly.

As shown in FIG. 9, a length L2 by which the coloring rod 110 of the practice device in this embodiment protrudes from the angle clamping member 600 is smaller, an angle V3 between the coloring rod 110 and the drawing medium E is more required to be infinitely close to 90 degrees. In other words, only when a requirement for the verticality is higher, the coloring rod can easily dispense pigment when in contact with the drawing medium E, which is also conducive to high standard training of the trainee for verticality feel.

As shown in FIG. 10, the length by which the coloring portion 100 of the tattoo practice device in the figure protrudes from the angle clamping member 600 is small. When an angle V4 between the coloring portion 100 and the drawing medium E is far from 90 degrees, the coloring portion 100 cannot fully come into contact with the drawing medium E, and drawing practice cannot be performed. This can prompt the operator to adjust a training degree in time, to train the verticality feel of the trainee.

Embodiment 5

Figure 12:
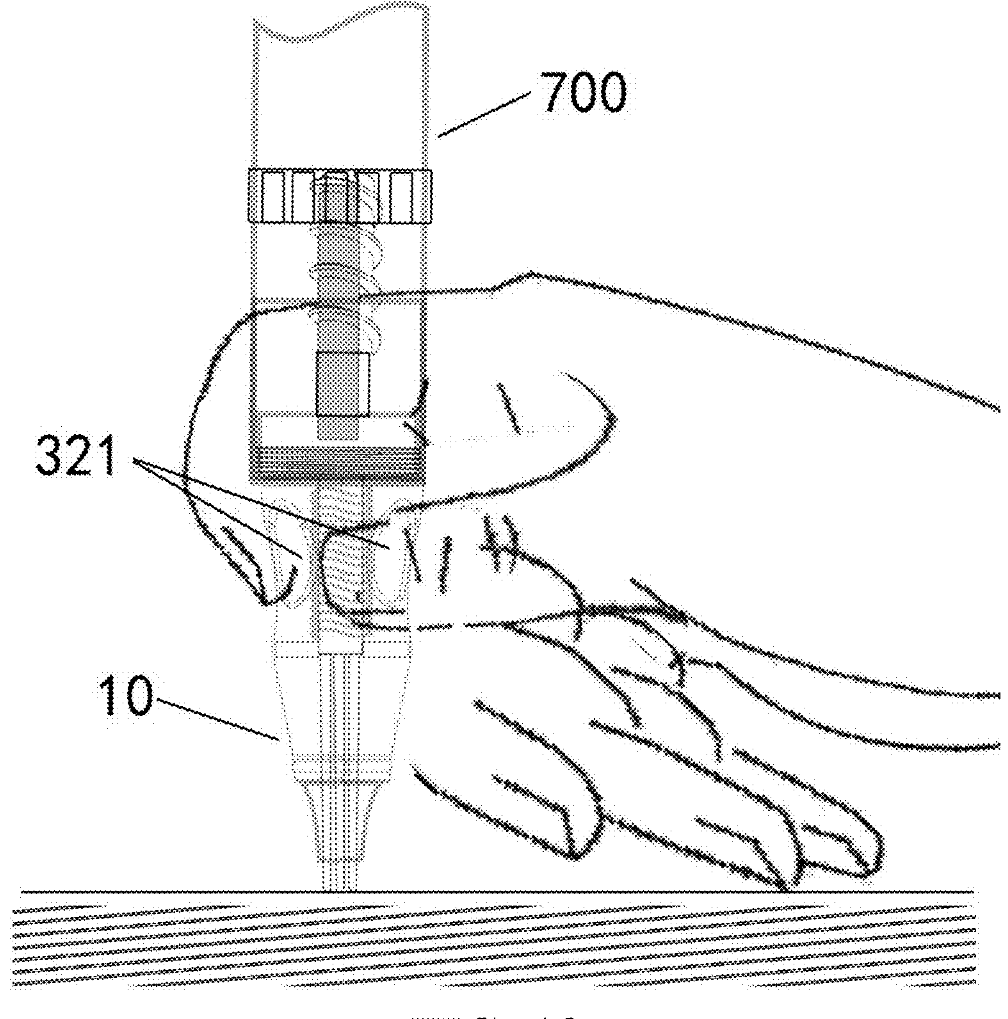
FIG. 12 is a diagram of a use state of using the tattoo practice device shown in FIG. 11 to color perpendicularly.

This embodiment provides a tattoo practice device 10. Referring to FIG. 11, the practice device includes a coloring portion 100. The coloring portion 100 includes three coloring rods 110 arranged in a single row. The three coloring rods 110 are HB leads with a thickness of 0.7 mm. The practice device further includes a connecting rod 210 connected to the coloring portion and a sleeve 300 sleeved on a periphery of the coloring portion 100 and the connecting rod 210. Two limiting holes 410, a spring 500 sleeved on the connecting rod 210 and having an end portion abutting against the structure inside the sleeve, and an angle clamping member 600 arranged at an outlet end 330 of the sleeve 300 are further arranged in the sleeve 300. The angle clamping member 600 in FIG. 11 may be actually understood as a clamping tube. The clamping tube is sleeved on a periphery of the coloring rod, and may limit an inclination angle of the coloring rod, and limit an extended length of the coloring rod. Further, in FIG. 11, a dent 321 is further provided on the sleeve 300. The dent 321 can increase friction force when the sleeve 300 is held. As shown in FIG. 12, the trainee's finger pads and finger joints can fit the dent 321 to prevent affecting practicing a high-verticality technique of the trainee due to tipping and sliding under power of the operation pen.

Certainly, to increase the friction force of the sleeve, corresponding structural design may also be performed according to a handheld gesture, such as arranging protrusions and ring belt strips or sleeving an anti-slip elastic ring at a handheld position.

In conclusion, the tattoo practice device provided in the present invention may be used as an aid for a tattooist to train tattooing feel and obtain a muscle memory. The practice device can simulate a movement state of the tattoo tool on a medium other than human skin, so that a user can experience a sense of using the tattoo tool in hands-on operation, and then enter a tattoo hands-on operation state as soon as possible. A tattooing feel and a muscle memory obtained in this hands-on operation state are fully matched with tattoo skills in hands-on operation, and have a perfect experience transfer characteristic. Compared with the existing common stationery drawing, the tattoo practice device provided in the present invention can shorten a skill acquisition time of the tattooist, and simulate a use state of the tattoo tool in the hands-on operation, and then the tattooist can quickly obtain the feel and the muscle memory that can be directly applied to the tattoo hands-on operation.

Further, Compared with static drawing tools such as pencils, brushes, pens, and gel ink pens, which are used in the industry today, the tattoo practice device provided in the present invention is equipped with a structure that can reciprocate, so that the nib (coloring portion) is in a reciprocating state during coloring, and the practice device is designed by simulating a coloring principle of the tattoo tool, helping the trainee adapt to a dynamic operation environment of the tattoo tool more directly and rapidly, thereby adapting to the tattoo tool in the hands-on operation state and increasing the excellent rate of the tattoo drawing.

Further, the tattoo practice device provided in the present invention is equipped with an end coloring portion that directly dispenses ink or pigment, so that the practice device can be used to directly draw on a non-human skin medium such as paper. There is no need to dab and mop the pigment, which saves overflowing ink and spraying the pigment, or staining the practice medium, the environment, and the trainee, and there is no need to prepare a variety of tattoo tools such as artificial human skins, tattoo needles, tattoo pigment, pigment cups, pigment holders, and skin oil. The practice device is clean and hygienic and easy to carry, and it can be used for tattoo practice anytime and anywhere to develop the feel and the muscle memory, shorten the learning process, and increase the completion rate and the excellent rate of the hands-on operation.

Further, the best coloring technique for tattooing requires a tool to vertically pierce the skin. Therefore, to adapt to this best coloring technique, the tattoo practice device provided in the present invention is equipped with the angle clamping member, which can control verticality required by the coloring portion (nib) during coloring by adjusting a position difference between a clamping position and the nib, to assist the tattoo trainee to train the degree of control over the verticality of the tool during tattoo coloring.

Further, the tattoo practice device provided in the present invention includes a limiting structure for enhancing stability of the coloring portion during coloring, which is easy for a beginner to start. In addition, because the design of the limiting structure makes the degree of swinging of the coloring portion of the practice device during drawing similar to the degree of swinging of a needling portion of the tattoo tool during needling, so that a pen handling feel of the practice device is closer to a pen handling feel of a professional tattoo tool used in the hands-on operation.

Further, the tattoo practice device provided in the present invention may also be combined and mounted with a tattoo operation pen, to restore a working environment close to the tattooist using the tattoo tool to tattoo the human skin, helping the tattooist adapt to the hands-on operation environment and train to master tattoo skills.

Embodiment 6

In the industry today, there is a lack of specialized practice tools before hands-on operation for machine tattooing, which are used for pre-practice to accumulate the most effective hands-on operation experience.

In the industry today, ordinary stationery pens are directly used on paper for practice, or a tattoo needle is directly used to be mounted on a machine for practice on the artificial skin, both having serious defects.

The former is using the ordinary stationery pens, such as pencils, brushes, pens, and gel ink pens, on the paper for tattoo operation pre-practice in teaching. Although pencils are usually used for practice, as opposed to professional machine tattoo needles, the nib of the ordinary stationery pens is static relative to the human hand during use. After connected to the machine, a coloring tip of the tattoo needle performs a striking movement up and down repeatedly. Therefore, the former is static and the latter is dynamic in coloring principle, and they differ in the holding gesture, angle of handling the pen, and strength control. As a result, the feel acquired through practice by using ordinary stationery pens mismatches the feel required in hands-on machine tattooing. The latter is directly using the tattoo needle to pre-practice on the artificial skin, and also has many defects:

First, safety is low. A beginner does not have the feel of using a dynamic tool to draw, and unsafe accidents such as getting hurt often occur because of directly using the tattoo needle.

Second, material and time costs are high. Various materials such as artificial skins, the tattoo needles, the tattoo pigments, the pigment cups, the pigment holders, the skin oil, skin wiping cotton, and gloves need to be prepared for practice. The artificial skin is tough and tensile, and does not have stable adhesion for ink, the tattoo needle needs to be dipped in the pigment and pierce the artificial skin for coloring, and cleaning oil is used to repeatedly scrub the artificial skin for cleaning floating color on the surface, to observe a coloring effect. An action of dot piercing or line drawing for coloring takes only a few seconds, but a process of cleaning the floating color on the artificial skin takes a few minutes. In an hour of practice, most of time is spent on cleaning, leading to the high costs and low efficiency.

Third, it is easy to misjudge a practice effect. Since a thickness of a conventional tattoo needle is in a range of 0.18 mm to 0.30 mm, whether the needle pierces the artificial skin perpendicularly or aslant, a small colored point is formed on the surface of the artificial skin. Alternatively, since the hand is not stable in a practice stage, the needle is inserted by different depths in a same practice stage, forming small colored points on the surface of the artificial skin. A difference between shapes of the colored points is not large, and it is difficult to determine whether the practice action is correct from the shapes of the colored points on the surface with the naked eyes. In addition, the shapes of the colored points on the surface may deform and become smaller due to a contraction force of the surface of the artificial skin. It is difficult to distinguish with the naked eyes, causing the practice effect to be misjudged. The incorrect action cannot be corrected in time, or is even accumulated to form a habit that is difficult to correct. If such practice experience is transferred to hands-on operation, it is easy cause a failure of tattooing, and it is difficult to trace back to the root cause of the problem, frustrating the trainee, and reducing the completion rate.

In conclusion, effective machine tattoo pre-practice is practice in which whether an angle of the piercing action is perpendicular and the strength is stable can be clearly checked in time. Under the guidance of the trainer, the trainee can perform self-check and self-correction, to discover mistakes in time and correct mistakes in time, reduce learning and teaching costs, and improve the completion rate. An effective tattoo pre-practice tool is not a tattoo hands-on operation tool, but a transition physical object providing an environment close to the hands-on operation environment, effectively accumulating a positive practice effect, thereby ensuring safe and effective hands-on operation after the tattoo tool is replaced.

Moreover, after the coloring portion is worn out or broken, the entire tattoo practice device can only be replaced, leading to high costs. In addition, after the coloring portion is worn out, during practice, it is difficult to observe whether pattern drawing is perpendicular to the paper, causing a poor practice effect. Even if the gesture is incorrect, it is difficult to correct, affecting the learning effect.

Figure 13:
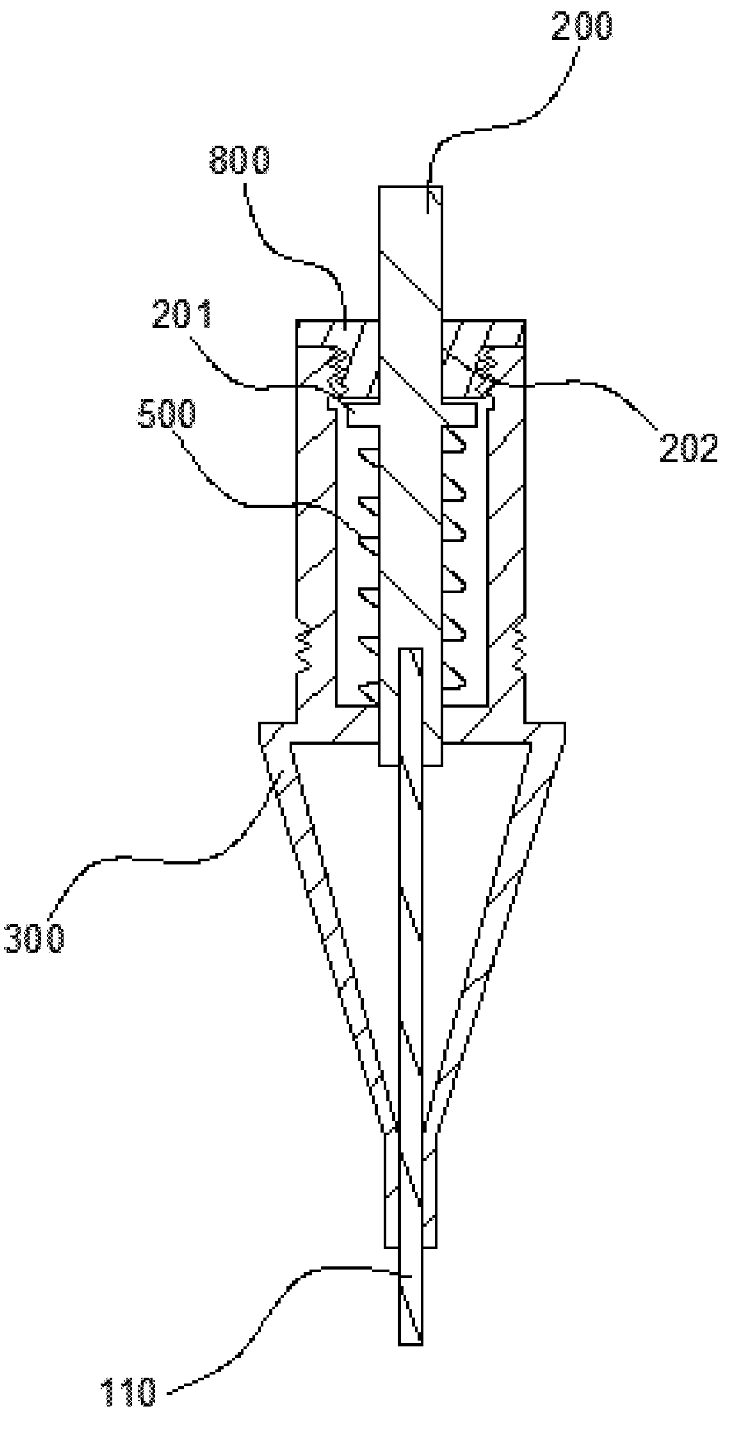
FIG. 13 is a schematic structural diagram of a tattoo practice device including a splitting portion according to the present invention.

Therefore, this embodiment provides a tattoo practice device. Referring to FIG. 13, a splitting portion 800 is detachably mounted on the top of the sleeve, and the top of the connecting portion runs through the splitting portion and is arranged above the splitting portion. In a state that the splitting portion is mounted on the sleeve, the splitting portion limits a space for an upward movement of the connecting portion, making the connecting portion and the lead core fail to be separated from the sleeve; and in a state that the splitting portion is detached from the sleeve, the splitting portion releases limitation on the upward movement of the connecting portion, enabling the connecting portion and the lead core to be separated from the sleeve from the top of the sleeve.

A resilient anti-splitting member 201 is arranged on an outer surface of a middle portion of the connecting portion, an anti-splitting hole 202 is provided on a middle portion of the splitting portion, and the top of the connecting portion runs through the anti-splitting hole and is arranged right above the splitting portion. The resilient anti-splitting member is arranged in the sleeve below the anti-splitting hole, and an outer diameter of the resilient anti-splitting member is greater than a diameter of the anti-splitting hole. The bottom of the elastic member abuts against an inner wall of the sleeve, the top of the elastic member abuts against a bottom surface of the resilient anti-splitting member, and the elastic member pushes the resilient anti-splitting member, the connecting portion, and the lead core to move upward, so that a top surface of the resilient anti-splitting member abuts against a bottom surface of the splitting portion.

The operation penholder and the sleeve or the splitting portion are used for connection, and the connecting portion and the lead core are driven to move up and down by operating the driving member on the handle. During practical use, the lead core moves up and down, and colors the paper, and the operator holds the operation penholder to drive the practice device to move on the paper. In this process, the lead core draws corresponding figures on the paper. In addition, each time the lead core comes into contact with the paper, one colored point is formed. If the lead core is perpendicular to the paper, the colored point is a circular dot or is approximately a circular dot. If the pen is handled aslant, the lead core draws a long dotted colored point on the paper, which has a large difference from a circular dotted colored point. The trainee and the trainer can easily determine whether the angle of the trainee handling the pen is perpendicular from the shape of the colored point on the paper. This is conducive to timely correction of mistakes for the trainee and the trainer, and has a function of checking correctness of practice actions, thereby improving efficiency of effective practice, and further improving the completion rate and excellent rate. Moreover, because the splitting portion is detachably connected to the sleeve, after the lead core is abraded for a period of time and can no longer be used, or after the lead core is broken, the splitting portion can be detached from the sleeve, and the lead core and connecting portion can be detached for replacement, or only the lead core is detached from the connecting portion for replacement. In this way, there is no need to replace the entire practice device, which can effectively reduce the learning costs.

Therefore, the lead core is directly used in the present invention. In this way, during practice, the lead core does not have piercing function, and is used for dynamic coloring practice on the paper, preventing the beginner from accidental piercing and accidental injuries caused by directly using the needle to practice on the artificial skin, when the beginner does not have a drawing feel in the dynamic environment. This improves safety of the trainee.

The lead core is used in the present invention, and the elastic member is arranged to weaken a force applied by the lead core on the paper, the lead core does not have piercing function on the paper to be colored, and a diameter of the lead core is greater than a diameter of a conventional tattoo needle. In this way, a surface of the paper is colored clearly, providing a function of checking correctness of practice operations by using the colored points. Tattoo practice requires dot piercing practice, which requires a perpendicular needle piercing angle. If the tattoo needle is used for practice, since the needle tip has piercing function, whether the needle pierces the artificial skin perpendicularly or aslant, a colored point less than 1 mm is formed on the surface. A difference between shapes of the colored points is not large, and it is difficult for the operator and the trainer to determine whether the angle of the trainee handling the pen is correct from the colored point on the surface. However, the lead core in the present invention does not have piercing function, during practice on the paper, if the pen is handled aslant, the lead core draws a long dotted colored point on the paper, which has a large difference from a circular dotted colored point. The trainee and the trainer can easily determine whether the angle of the trainee handling the pen is perpendicular from the shape of the colored point on the paper. This is conducive to timely correction of mistakes for the trainee and the trainer, and has a function of checking correctness of practice actions, thereby improving efficiency of effective practice, and further improving the completion rate and excellent rate.

A detachable splitting portion is arranged on the sleeve in the present invention. When detached from the sleeve, the splitting portion can release limiting on the connecting portion and the lead core. In this way, when the lead core is broken or worn out, the lead core or the connecting portion can be directly replaced, which can further reduce practice costs. In addition, after the lead core is worn out, if whether the worn out lead can be used for practice cannot be correctly determined, a lead with a proper length is replaced immediately, which further improves stability of the practice, and helps to determine whether the angle of the trainee handling the pen is perpendicular, facilitating timely correction for the trainee and the trainer, improving practice efficiency, and reducing practice costs.

Figure 14:
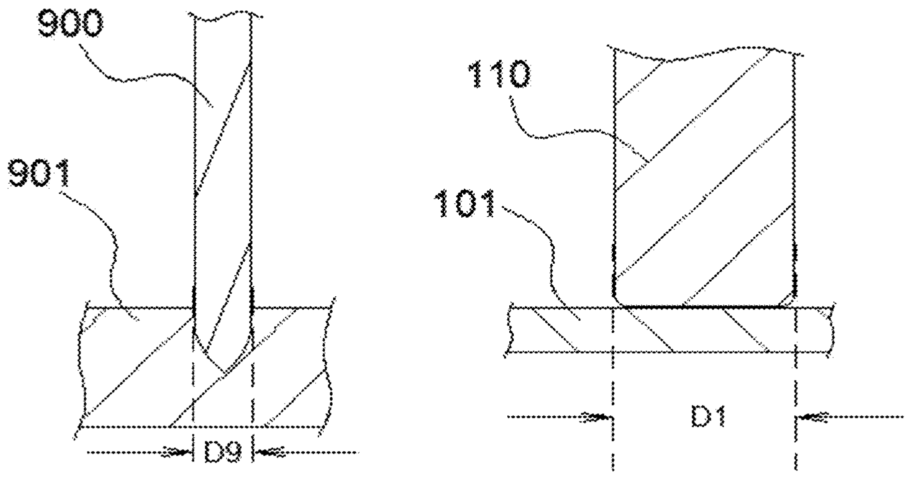
FIG. 14 is a structural diagram of comparison of using a tattoo needle to color an artificial skin and using a lead to color paper according to the present invention.

Referring to FIG. 14, a lead 110 coloring on paper 101 is compared with a tattoo needle 900 piercing on an artificial skin 901. It is assumed that the lead core and the tattoo needle are both practiced in a perpendicular state, a diameter D1 of the lead core is 1.0 mm, and a diameter D9 of the tattoo needle is 0.25 mm. The lead core does not have piercing function for the paper, and the tattoo needle has piercing function for the artificial skin. When the lead core is used for practice, the lead core abuts on the paper to implement dotted coloring, and when the tattoo needle is used to pierce the artificial skin, the tattoo needle pierces a hole on the artificial skin.

Figure 15:
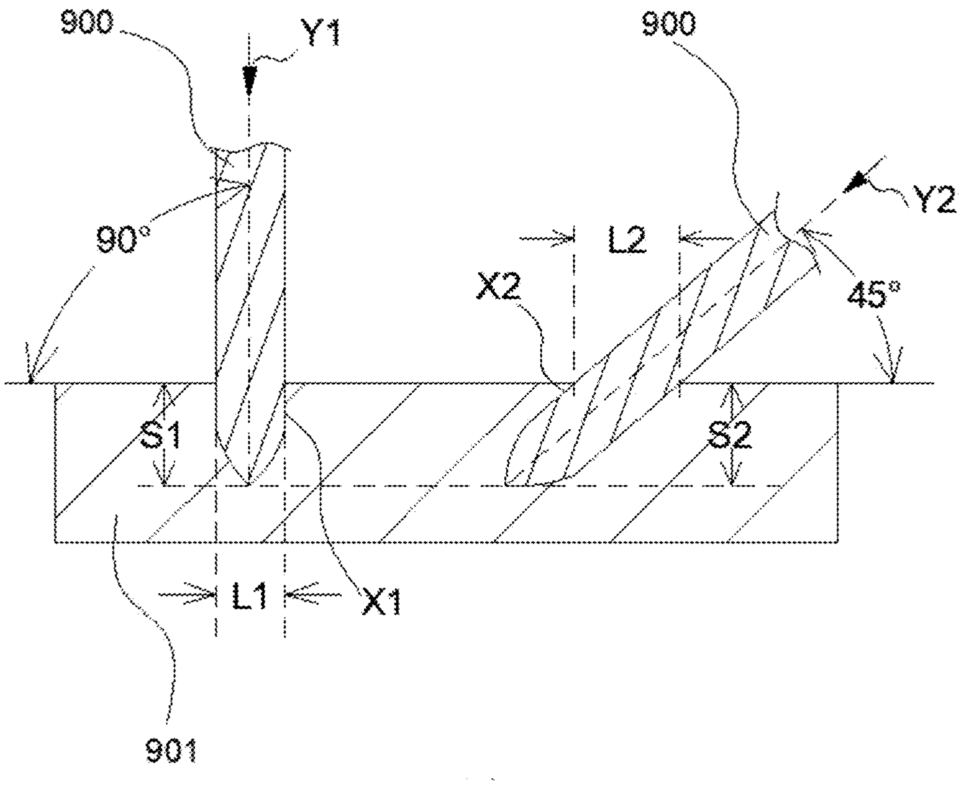
FIG. 15 is a schematic structural diagram of comparison of using a tattoo needle to pierce an artificial skin in a perpendicular form and in an inclined form according to the present invention.

Referring to FIG. 15, as a comparison, if the tattoo needle is used to practice piercing on the artificial skin, the tattoo needle pierces the artificial skin in a direction Y1. Y1 is perpendicular to the artificial skin, and a piercing depth is S1. In this way, a maximum diameter of a visible colored point X1 on the surface of the artificial skin is L1. When the tattoo needle pierces the artificial skin in a direction Y2, Y2 is inclined to the artificial skin. An angle between the tattoo needle and the artificial skin is 45°, and a piercing depth is S2. In this way, a maximum diameter of a visible colored point X2 on the surface of the artificial skin is L2. When S1=S2, a difference between L1 and L2 is 0.1 mm. In this way, when the tattoo needle pierces the artificial skin perpendicularly and at an angle of 45°, the difference between the maximum diameters of the visible colored points on the surface of the artificial skin is only about 0.1 mm, which is difficult to distinguish with the naked eyes.

Figure 16:
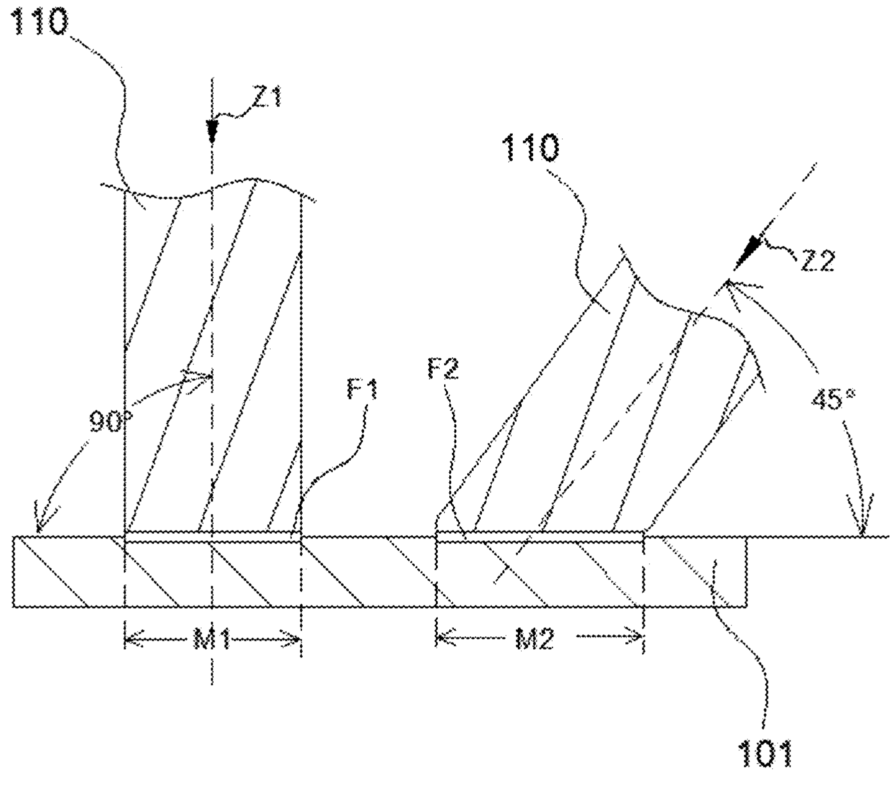
FIG. 16 is a schematic structural diagram of comparison of using a lead to color paper in a perpendicular form and in an inclined form according to the present invention.

Referring to FIG. 16, the lead core is used to practice coloring on the surface of the paper. The lead core pierces the paper in a direction Z1 for the first time, and Z1 is perpendicular to the paper. Because the lead core does not have piercing function for the paper, the lead core strikes the paper in a dot piercing manner to color the paper. The lead core is abraded and colors the paper, leaving a colored point F1. A maximum diameter of the colored point F1 visible on the surface is M1. When the lead core pierces the paper in a direction Z2, an angle between Z2 and the paper is 45°. Because the lead core does not have piercing function, when the lead core strikes the paper in a dot piercing manner, the lead core is abraded and colors the paper, forming a colored point F2 on the paper with a maximum diameter of M2. A difference between M1 and M2 is about 0.4 mm, which is easy to distinguish with the naked eyes. Therefore, using the lead core to practice coloring on the paper is compared with using the tattoo needle to practice coloring on the artificial skin. When the angle is inclined, a maximum diameter error between an incorrect colored point and a correct colored point is clearer, and it is easier to determine through a difference between the colored points on the paper whether the coloring action is perpendicular. This can improve convenience and quality of the practice, and facilitate correction of an incorrect action. In addition, a cost of the paper is lower than a cost of the artificial skin, and it is convenient to determine whether the action of the trainee is correct.

Self-checking accuracy is performed through the following comparison: 20 experimenters, aged 20 to 45, with no experience in tattoo practice or hands-on operation, are divided into two groups, A1 and A2, with 10 participants in each group;

First Time:

In group A1, a tattoo needle is used to practice dot piercing on an artificial skin, adapting to a tattoo machine, which has a weight of 55 g, a motor power of 5 W, and a speed of 3600 RPM (3600 revolutions per minute).

In group A2, a tattoo practice device in this application is used to practice dot piercing on paper, adapting to a practice pen that has same parameters as the tattoo machine of group A1, which has a weight of 55 g, a motor power of 5 W, and a speed of 3600 RPM (3600 revolutions per minute).

After the same instruction of the trainer on how to determine whether a dot piercing angle is perpendicular by a difference between shapes of the colored points on the surface of the coloring medium, experiments are conducted in groups.

Processes of dot piercing practice in both groups are recorded with multi-angle video filming to play back slow motion to check whether each dot piercing movement is perpendicular to the artificial skin or the paper.

In group A1, the 10 experimenters use the tattoo needles to practice dot piercing on the artificial skin, and each experimenter dot-pierces 100 points, leading to a total of 1,000 points. In group A1, the experimenters perform self-checking according to colored points visible on the surface of the artificial skin, to obtain that the number of non-perpendicular points is 105, and the actual number of non-perpendicular points according to video playback is 543, with an accuracy of 19.3%.

In group A2, the 10 experimenters use the tattoo practice device to practice dot piercing on the paper, and each experimenter dot-pierces 100 points, leading to a total of 1,000 points. In group A2, the experimenters perform self-checking according to colored points visible on the surface of the paper, to obtain the number of non-perpendicular points is 355, and the actual number of non-perpendicular points according to video playback is 362, with an accuracy of 98.1%.

Second Time:

In group A2, a tattoo needle is used to practice dot piercing on an artificial skin, adapting to a tattoo machine, which has a weight of 55 g, a motor power of 5 W, and a speed of 3600 RPM (3600 revolutions per minute).

In group A1, a tattoo practice device in this application is used to practice dot piercing on paper, adapting to a practice pen that has same parameters as the tattoo machine of group A2, which has a weight of 55 g, a motor power of 5 W, and a speed of 3600 RPM (3600 revolutions per minute).

After the same instruction of the trainer on how to determine whether a dot piercing angle is perpendicular by a difference between shapes of the colored points on the surface of the coloring medium, experiments are conducted in groups.

Processes of dot piercing practice in both groups are recorded with multi-angle video filming to play back slow motion to check whether each dot piercing movement is perpendicular to the artificial skin or the paper.

In group A2, the 10 experimenters use the tattoo needles to practice dot piercing on the artificial skin, and each experimenter dot-pierces 100 points, leading to a total of 1,000 points. In group A2, the experimenters perform self-checking according to colored points visible on the surface of the artificial skin, to obtain that the number of non-perpendicular points is 42, and the actual number of non-perpendicular points according to video playback is 150, with an accuracy of 28.0%.

In group A1, the 10 experimenters use the tattoo practice device to practice dot piercing on the paper, and each experimenter dot-pierces 100 points, leading to a total of 1,000 points. In group A1, the experimenters perform self-checking according to colored points visible on the surface of the paper, to obtain that the number of non-perpendicular points is 277, and the actual number of non-perpendicular points according to video playback is 294, with an accuracy of 94.2%.

Data comparison is shown in the following table.

| Practice tool | Experimenter | Number of non-perpendicular points through self-checking | Actual number of non-perpendicular points | Accuracy |
|---|---|---|---|---|
| Tattoo needle | Group A1 | 105 | 543 | 19.3% |
| | Group A2 | 42 | 150 | 280% |
| Tattoo practice device | Group A2 | 355 | 362 | 98.1% |
| | Group A1 | 277 | 294 | 94.2% |

Figure 17:
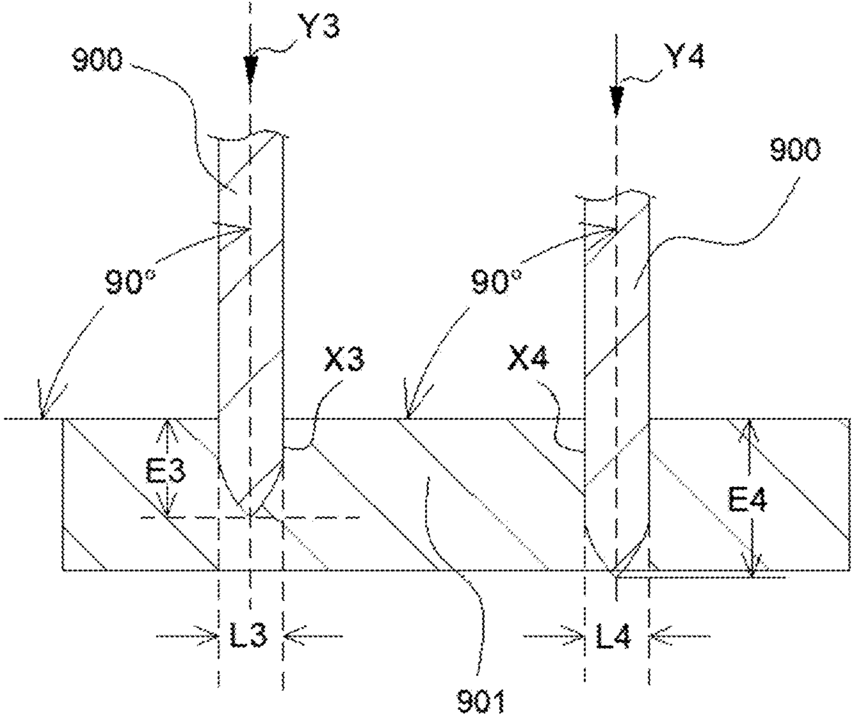
FIG. 17 is a schematic structural diagram of comparison of different strengths of using a tattoo needle to pierce an artificial skin in a perpendicular form according to the present invention.

Referring to FIG. 17, as a comparison, for example, the tattoo needle is used to pierce the artificial skin. The tattoo needle pierces the artificial skin in a direction Y3 with a standard strength, Y3 is perpendicular to the artificial skin, the piercing depth is E3, and a maximum diameter of a colored point X3 visible on the surface of the artificial skin is L3. The tattoo needle pierces the artificial skin in a direction Y4 with a large strength, Y4 is also perpendicular to the artificial skin, the piercing depth is E4, E4 is greater than a thickness of the artificial skin, a maximum diameter of a colored point X4 visible on the surface of the artificial skin is L4, and L3=L4. In this way, when the tattoo needle is used to practice piercing on the artificial skin, strengths are different, and if the strength is excessive, the artificial skin may be pierced through. The maximum diameter of the colored point visible on the surface of the artificial skin is substantially the same as the diameter of the colored point piercing the artificial skin with the standard strength, with no difference. Therefore, whether the strength of the tattoo needle piercing the artificial skin is uniform cannot be determined. In addition, because the tattoo needle has piercing function for the artificial skin, in a practical case, similar to perforation coloring, even if the strengths are different, a formed hole depth E3 is not equal to E4, formed ink falls into the hole formed by piercing and forms a thick accumulation, and it is difficult to distinguish from the surface of the artificial skin through a visual concentration. In addition, even if the strength is large, and there is much ink accumulated around the colored point formed by piercing the surface of the artificial skin, because the surface of the artificial skin is smooth, and does not have adhesion for the ink, the ink disappears after being wiped with cleaning oil, and a determining basis cannot be formed.

However, tattooing hands-on operation requires a uniform strength, to deliver the pigment to a same depth under the skin, avoiding subsequently uneven color retention or contour deformation due to inconsistent metabolic rates. Therefore, in a stage of strength uniformity practice, the trainee cannot perform self-checking and self-correction in time by using the tattoo needle.

Figure 18:
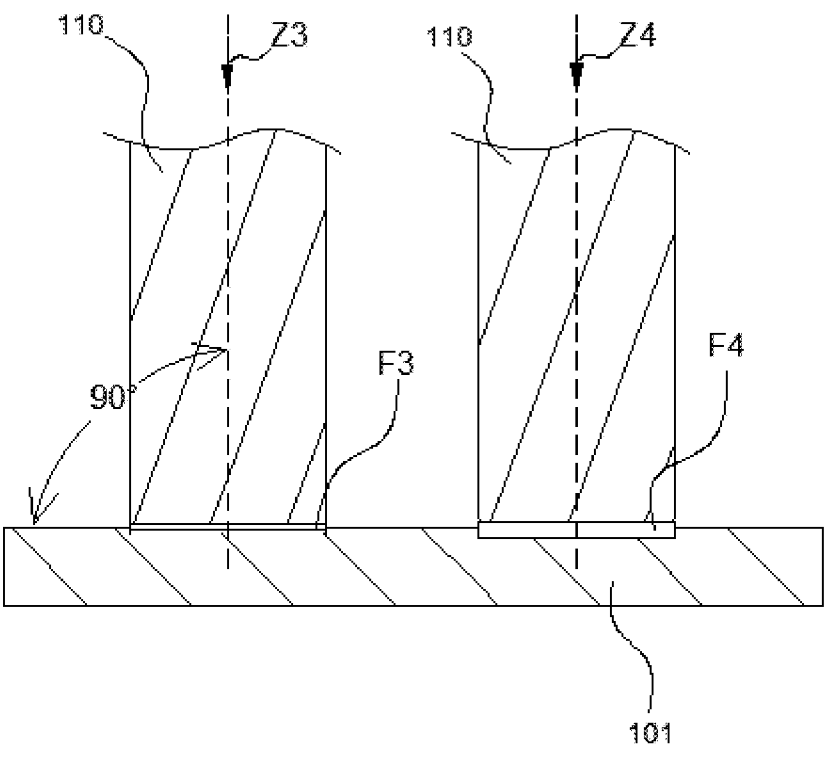
FIG. 18 is a schematic structural diagram of comparison of different strengths of using a lead to strike paper in a perpendicular form according to the present invention.
Figure 19:
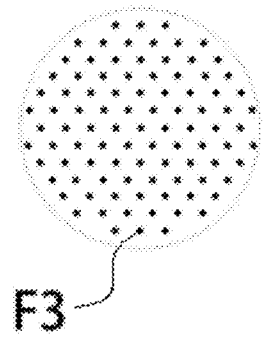
FIG. 19 is a schematic structural diagram of comparison of colored points with different strengths of using a lead to strike paper in a perpendicular form according to the present invention.
Figure 19:
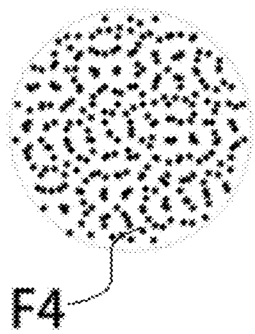

Referring to FIG. 18, the lead core is used to practice on the paper. The lead core strikes the paper in a direction Z3 with the standard strength, and Z3 is perpendicular to the paper. When the lead core strikes the paper for coloring in a dot piercing manner, the lead core is abraded and leaves a colored point F3. The lead core strikes the paper in a direction Z4 with a larger strength, and Z4 is perpendicular to the paper. When the lead core strikes the paper for coloring in a dot piercing manner, the lead core is abraded in a greater degree than striking with the standard strength, coloring the paper with more carbon powder and larger density. A colored point on the paper is F4, the colored point F4 has a deeper color. Different strengths indicate different accumulation densities of carbon powder and different visual concentrations at the colored points F3 and F4. Referring to FIG. 19, one side is the colored point F3, and the other side is the colored point F4. Therefore, during strength uniformity practice, when the strength suddenly increases or decreases, the colored points on the paper also suddenly become thicker or lighter, which is easier for distinguishing. In this way, compared with using the tattoo needle to practice on the artificial skin, using the lead core to practice strength on the paper is easier for distinguishing whether the strength is uniform, thereby improving the practice effect.

In summary, the present invention provides a tattoo practice device. The practice device may be used as an aid for a tattooist to train a tattooing feel and obtain a muscle memory. The practice device can simulate a movement state of the tattoo tool on a medium other than human skin, so that a user can experience a sense of using the tattoo tool in hands-on operation, and then enter a tattoo hands-on operation state as soon as possible. A tattooing feel and a muscle memory obtained in this hands-on operation state are fully matched with tattoo skills in hands-on operation, and have a perfect experience transfer characteristic. Compared with the existing common stationery drawing, the tattoo practice device provided in the present invention can shorten a skill acquisition time of the tattooist, and simulate a use state of the tattoo tool in the hands-on operation, and then the tattooist can quickly obtain the feel and the muscle memory that can be directly applied to the tattoo hands-on operation.

Compared with static drawing tools such as pencils, brushes, pens, and gel ink pens, which are used in the industry today, the tattoo practice device provided in the present invention is equipped with a structure that can reciprocate, so that the nib (coloring portion) is in a reciprocating state during coloring, and the practice device is designed by simulating a coloring principle of the tattoo tool, helping the trainee adapt to a dynamic operation environment of the tattoo tool more directly and rapidly, thereby adapting to the tattoo tool in the hands-on operation state and increasing the excellent rate of the tattoo drawing.

The tattoo practice device provided in the present invention is equipped with an end coloring portion that directly dispenses ink or pigment, so that the practice device can be used to directly draw on a non-human skin medium such as paper. There is no need to dab and mop the pigment, which saves overflowing ink and spraying the pigment, or staining the practice medium, the environment, and the trainee, and there is no need to prepare a variety of tattoo tools such as artificial human skins, tattoo needles, tattoo pigment, pigment cups, pigment holders, and skin oil. The practice device is clean and hygienic and easy to carry, and it can be used for tattoo practice anytime and anywhere to develop the feel and the muscle memory, shorten the learning process, and increase the completion rate and the excellent rate of the hands-on operation.

The best coloring technique for tattooing requires a tool to vertically pierce the skin. Therefore, to adapt to this best coloring technique, the tattoo practice device provided in the present invention is equipped with an angle clamping member, which can control verticality required by the coloring portion (nib) during coloring by adjusting a position difference between a clamping position and the nib, to assist the tattoo trainee to train the degree of control over the verticality of the tool during tattoo coloring.

The tattoo practice device provided in the present invention includes a limiting structure for enhancing stability of the coloring portion during coloring, which is easy for a beginner to start. In addition, because the design of the limiting structure makes the degree of swinging of the coloring portion of the practice device during drawing similar to the degree of swinging of a needling portion of the tattoo tool during needling, so that a pen handling feel of the practice device is closer to a pen handling feel of a professional tattoo tool used in the hands-on operation.

In the descriptions of this specification, a description of a reference term such as "an embodiment", "some embodiments", "an example", "a specific example", or "some examples" means that a specific feature, structure, material, or characteristic that is described with reference to the embodiment or the example is included in at least one embodiment or example of the present invention. In this specification, schematic descriptions of the foregoing terms are not necessarily directed at the same embodiment or example. Moreover, the specific features, structures, materials, or characteristics described may be combined in any one or more embodiments or examples in an appropriate manner. In addition, a person in the art may combine different embodiments or examples described in this specification.

Although the embodiments of the present invention have been shown and described above, it can be understood that, the foregoing embodiments are exemplary and should not be understood as limitation to the present invention. A person of ordinary skill in the art can make changes, modifications, or variations to the foregoing embodiments within the scope of the present invention.

What is claimed is:

1. A tattoo practice device, comprising a coloring portion, a connecting portion, and a sleeve, wherein the coloring portion comprises a coloring rod, wherein the coloring rod is a coloring core configured to apply a color on a drawing medium; the coloring rod comprises a non-piercing distal end;

one end of the connecting portion is connected to the coloring portion, the connecting portion is linked with the coloring portion, and the sleeve is sleeved on a periphery of the connecting portion;

the connecting portion is configured to move in a first direction along a central axis of the sleeve, so that the coloring core is close to the drawing medium and color the drawing medium; and the connecting portion is configured to move in a second direction opposite to the first direction along the central axis of the sleeve, so that the coloring core moves away from the drawing medium;

wherein the sleeve is a tubular sleeve, the sleeve has a fastening end, a middle connecting tube, and an outlet end; the fastening end, the middle connecting tube, and the outlet end are sequentially connected to form a channel for the connecting portion to reciprocate, and a central axis of the fastening end and a central axis of the middle connecting tube separately coincide with the central axis of the sleeve;

the fastening end is capable of being detachably connected to an external driving member, and an outlet is provided at the outlet end.

2. The tattoo practice device according to claim 1, further comprising an elastic member, arranged inside the sleeve, wherein, when the connecting portion is driven by an external force to move along the central axis of the sleeve to an outlet end of the sleeve close to the coloring portion, the elastic member elastically deforms to generate a restoring force; and when the external force applied to the connecting portion is released, the elastic member is configured to apply the restoring force to cause the connecting portion to restore to an initial position.

3. The tattoo practice device according to claim 2, further comprising an angle clamping portion, wherein the angle clamping portion is arranged on the outlet end of the sleeve close to the coloring portion;

when the coloring rod is driven with the connecting portion to move to the outlet end of the sleeve, an outer wall of the coloring rod abuts against the angle clamping portion, and the angle clamping portion limits an inclination angle of the coloring rod relative to the central axis of the sleeve; and the angle clamping portion limits a length of the coloring rod protruding out of the angle clamping portion; wherein the angle clamping portion and the sleeve are integrally formed as a one-piece structure or are separatable elements.

4. The tattoo practice device according to claim 1, wherein the coloring portion further comprises a mounting base, and the coloring rod is mounted to the mounting base;

a central axis of the coloring rod is parallel to an axial direction of the mounting base;

the coloring rod is an elongated columnar structure, and two end surfaces of the elongated columnar structure have a same shape and a same size; or the two end surfaces of the elongated columnar structure have different shapes and different sizes, and a size of one end surface close to the connecting portion is greater than a size of the other end surface.

5. The tattoo practice device according to claim 4, wherein the coloring portion and the connecting portion are in an integral design or a separate design;

the connecting portion comprises a connecting rod; and the connecting portion is capable of being connected to an external driving member, and the external driving member comprises at least one of a manual pen or an electric pen.

6. The tattoo practice device according to claim 1, wherein a handheld positioning portion is formed on the sleeve, the handheld positioning portion comprises at least one finger position point arranged on the middle connecting tube of the sleeve, and at least one dent is arranged in the middle connecting tube to form the at least one finger position point.

7. The tattoo practice device according to claim 1, wherein a limiting structure is arranged on the sleeve; the limiting structure is arranged in the middle connecting tube of the sleeve and/or on the fastening end of the sleeve and/or on the outlet end of the sleeve; and when the connecting portion reciprocates along the central axis of the sleeve, the connecting portion abuts against the limiting structure, and the limiting structure limits swinging of the connecting portion in a cross-sectional direction of the sleeve, to cause the connecting portion to drive the coloring rod of the coloring portion to vertically extend out of the sleeve until the coloring rod abuts against the drawing medium, and to cause the connecting portion to drive the coloring rod of the coloring portion to vertically retract from the outside of the outlet into the sleeve.

8. The tattoo practice device according to claim 7, wherein the limiting structure comprises a limiting hole and/or a limiting tube, wherein the limiting hole is provided with a through hole, and when the connecting portion reciprocates along the central axis of the sleeve, the connecting portion abuts against the through hole, and the through hole limits the swinging of the connecting portion in the cross-sectional direction of the sleeve; and the limiting tube has a channel, and when the connecting portion reciprocates along the central axis of the sleeve, the connecting portion abuts against the channel, and the channel limits the swinging of the connecting portion in the cross-sectional direction of the sleeve.

9. The tattoo practice device according to claim 1, wherein a splitting portion is detachably mounted on the top of the sleeve, and the top of the connecting portion runs through the splitting portion and is arranged above the splitting portion;

in a state that the splitting portion is mounted on the sleeve, the splitting portion limits a space for an upward movement of the connecting portion, making the connecting portion and the coloring core fail to be separated from the sleeve; and in a state that the splitting portion is detached from the sleeve, the splitting portion releases limitation on the upward movement of the connecting portion, enabling the connecting portion and the coloring core to be separated from the sleeve from the top of the sleeve.

10. A tattoo practice device, comprising a coloring portion, a connecting portion, and a sleeve, wherein the coloring portion comprises a plurality of coloring rods, wherein each of the plurality of coloring rods is a coloring core configured to apply a color on a drawing medium; each of the plurality of coloring rods comprises a non-piercing distal end;

one end of the connecting portion is connected to the coloring portion, the connecting portion is linked with the coloring portion, and the sleeve is sleeved on a periphery of the connecting portion;

the connecting portion is configured to move in a first direction along a central axis of the sleeve, so that the coloring cores are close to the drawing medium and color the drawing medium; and the connecting portion is configured to move in a second direction opposite to the first direction along the central axis of the sleeve, so that the coloring cores move away from the drawing medium;

wherein a splitting portion is detachably mounted on the top of the sleeve, and the top of the connecting portion runs through the splitting portion and is arranged above the splitting portion;

in a state that the splitting portion is mounted on the sleeve, the splitting portion limits a space for an upward movement of the connecting portion, making the connecting portion and the coloring cores fail to be separated from the sleeve; and in a state that the splitting portion is detached from the sleeve, the splitting portion releases limitation on the upward movement of the connecting portion, enabling the connecting portion and the coloring cores to be separated from the sleeve from the top of the sleeve.

11. The tattoo practice device according to claim 10, further comprising an angle clamping portion, wherein the angle clamping portion is arranged on an outlet end of the sleeve close to the coloring portion;

when the coloring rods are driven with the connecting portion to move to the outlet end of the sleeve, at least part of outer walls of the coloring rods abuts against the angle clamping portion, and the angle clamping portion limits an inclination angle of the coloring rods relative to the central axis of the sleeve; and the angle clamping portion limits a length of the coloring rods protruding out of the angle clamping portion; the angle clamping portion and the sleeve are integrally formed as a one-piece structure or are separatable elements.

12. The tattoo practice device according to claim 10, wherein the coloring portion further comprises a mounting base, and the coloring rods are mounted to the mounting base;

each coloring rod is an elongated columnar structure, and two end surfaces of the elongated columnar structure have a same shape and a same size; or the two end surfaces of the elongated columnar structure have different shapes and different sizes, and a size of one end surface close to the connecting portion is greater than a size of the other end surface.

13. A tattoo practice device, comprising a coloring portion, a connecting portion, and a sleeve, wherein the coloring portion comprises a coloring rod, wherein the coloring rod is a coloring core configured to apply a color on a drawing medium; the coloring rod comprises a non-piercing distal end;

one end of the connecting portion is connected to the coloring portion, the connecting portion is linked with the coloring portion, and the sleeve is sleeved on a periphery of the connecting portion;

the connecting portion is configured to move in a first direction along a central axis of the sleeve, so that the coloring core is close to the drawing medium and color the drawing medium; and the connecting portion is configured to move in a second direction opposite to the first direction along the central axis of the sleeve, so that the coloring core moves away from the drawing medium;

wherein a splitting portion is detachably mounted on the top of the sleeve, and the top of the connecting portion runs through the splitting portion and is arranged above the splitting portion;

in a state that the splitting portion is mounted on the sleeve, the splitting portion limits a space for an upward movement of the connecting portion, making the connecting portion and the coloring core fail to be separated from the sleeve; and in a state that the splitting portion is detached from the sleeve, the splitting portion releases limitation on the upward movement of the connecting portion, enabling the connecting portion and the coloring core to be separated from the sleeve from the top of the sleeve.

14. The tattoo practice device according to claim 13, wherein:

the tattoo practice device further comprises an elastic member connected to at least one of: the connecting portion, the coloring portion, or the splitting portion;

the splitting portion defines a through hole for movably mounting the connecting portion;

the coloring portion and the connecting portion are integrally formed as a one-piece structure or are two separatable elements; the connecting portion is movably received in the through hole of the splitting portion; when the connecting portion is driven by an external force to move along a central axis of the coloring portion, the elastic member is elastically deformed to generate a restoring force; and when the external force applied to the connecting portion is released, the elastic member is configured to apply the restoring force to cause the connecting portion to restore to an initial position.

15. The tattoo practice device according to claim 14, wherein the elastic member comprises at least one of a spring, a silicone member, or a rubber band.

16. The tattoo practice device according to claim 14, wherein the splitting portion, the connecting portion, the coloring portion, and the sleeve are coaxial.

17. The tattoo practice device according to claim 14, further comprising an anti-splitting member arranged on an outer surface of the connecting portion, wherein the anti-splitting member is arranged in the sleeve below the splitting portion, and an outer diameter of the anti-splitting member is greater than a diameter of the through hole of the splitting portion.

18. The tattoo practice device according to claim 13, wherein the sleeve is a tubular sleeve, the sleeve has a fastening end, a middle connecting tube, and an outlet end; the fastening end is capable of being detachably connected to an external driving member, and an outlet is provided at the outlet end, and the non-piercing distal end of the coloring rod is capable of extending out from the outlet or retracted into the sleeve via the outlet.

* * * * *